(12) United States Patent
Barham et al.

(10) Patent No.: US 6,784,345 B1
(45) Date of Patent: *Aug. 31, 2004

(54) HEAT TOLERANT BROCCOLI

(75) Inventors: Robert Barham, Gilroy, CA (US); David Joynt, Hollister, CA (US)

(73) Assignee: R&D AG, Inc., Gilroy, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/869,002

(22) PCT Filed: Dec. 29, 1999

(86) PCT No.: PCT/US99/31230

§ 371 (c)(1),
(2), (4) Date: Jun. 22, 2001

(87) PCT Pub. No.: WO00/38500

PCT Pub. Date: Jul. 6, 2000

Related U.S. Application Data
(60) Provisional application No. 60/114,038, filed on Dec. 29, 1998.

(51) Int. Cl.$^7$ .............................. A01H 5/00; A01H 5/10; A01H 1/00
(52) U.S. Cl. ....................................... 800/306; 800/260
(58) Field of Search .................. 800/260, 265–266, 800/268, 270, 276, 295, 299, 306; 435/420, 421, 430, 430.1

(56) References Cited

U.S. PATENT DOCUMENTS

| | | | |
|---|---|---|---|
| 5,731,505 A | 3/1998 | Sasayama et al. | ......... 800/200 |
| 6,294,715 B1 * | 9/2001 | Barham et al. | ............. 800/306 |

OTHER PUBLICATIONS

U.S. patent application Ser. No. 09/328,121, Barham et al., filed Jun. 8, 1999.
"Broccoli," World Wide Web Page: http://aggie–horticulture.tamu.edu/plantanswers/vegetables/broccoli.html, pp. 1–3.
Wing, Lucy, "Country Living: Lucy's Country Garden: Cultivating Broccoli,", World Wide Web Page: wysiwyg://217/http://homearts.com/cl/garden/03brogfl.htm, p. 1.
Bjorkman, Thomas et al., "The heat–sensitive stage of broccoli flower development," World Wide Web Page: http://www.nysaes.cornell.edu/hort/faculty/bjorkman/broccoli/broccoli.html, pp. 1–5.
Bjorkman, Thomas et al., "High temperature arrest of inflorescence development in broccoli (Brassica oleracea var. italica L.)," World Wide Web Page: http://www.nysaes.cornell.edu/hort/faculty/bjorman/other/abstracts/brocht.html, p. 1.
LeStrange, Michelle et al., "Broccoli Production in California," University of California, Division of Agriculture and Natual Resources, Publication 7211, pp. 1–3.
"Broccoli," World Wide Web Page: http://www.nysaes.cornell.edu/hor . . . /bjorkman/broccoli/broccoli2.html, p. 1 of.
McCandless, L., Breakthrough DNA Device for Plant Breeders Developed at Cornell's Geneva Experiment Station, pp. 1–2, Cornell University, World Wide Web Page: http://www.news.cornell.edu/releases/Nov98/MatrixMill.l-m.html.
Bjorkman, Thomas et al., "High temperature arrest of inflorescence development in broccoli (Brassica oleracea var. italica L.)," Journal of Experimental Botany, vol. 49, No. 318, pp. 101–106, (1998) (previously cited only the abstract–disclosed herewith in its entirety).
Heather, D. W., et al., "High Tolerance and Holding Ability in Broccoli", J. Amer. Soc. Hort. Sci. 117(6); pp. 887–892 (1992).
Dufault, R. J., "Dynamic Relationships Between Field Temperatures and Broccoli Head Quality", J. Amer. Soc. Hort. Sci. 121(4):705–710 (1996).
Yang, et al., "A Heat–Tolerant Broccoli $F_1$ Hybrid", Ching–Long 45, HortScience 33 (6) :1090–1091 (1998).
Sullivan, C.Y., et al., "Plant Responses to High Temperatures", Genetic Diversity in Plants, 28:301–317 (1976).
Robertson, et al., "Regeneration of Green Comet Broccoli From Mesophyll Protoplasts," Cruciferae Newsletter, Vol. No. 9, pp. 39–40, 1984.
PCT Search Report, PCT/US99/31230 (Int'l Filing Date: Dec. 29, 1999).

* cited by examiner

*Primary Examiner*—David T. Fox
*Assistant Examiner*—Cynthia Collins
(74) *Attorney, Agent, or Firm*—Morrison & Foerster LLP

(57) ABSTRACT

Heat tolerant broccoli plants and seed produced therefrom are described. The heat tolerant broccoli plants are capable of producing a commercially acceptable broccoli head under heat stress growth conditions. The heat tolerant broccoli plants are exemplified by seeds deposited with the American Type Culture Collection and having ATCC Accession numbers: 203530, 203531, 203532, and 203533.

8 Claims, 1 Drawing Sheet

HEAT TOLERANT BROCCOLI

CROSS REFERENCE TO RELATED APPLICATIONS

This application is a U.S. national phase application of International PCT/US99/31230, filed Dec. 29, 1999, which claims priority to U.S. application Ser. No. 09/328,121 filed Jun. 8, 1999, which claims priority to U.S. Provisional Application Ser. No. 60/114,038, filed Dec. 29, 1998, all of which are hereby incorporated by reference in their entirety.

FIELD OF THE INVENTION

This invention is in the field of plant breeding. In particular, this invention relates to the development of heat tolerant broccoli (*Brassica oleracea* L. var. *italica*).

BACKGROUND OF THE INVENTION

Broccoli (*Brassica oleracea* L. var. *italica*) has become an increasingly popular crop worldwide especially in health-conscious areas of the western world such as the North America, Europe, and Japan. An average broccoli stalk contains only 30 calories and provides 240% of the recommended daily allowance of vitamin C plus 10% of the recommended daily allowance of vitamin A. In addition to its nutritional value, some recent studies have shown that broccoli aids in the prevention of some forms of cancer.

Broccoli is a cool weather crop. High temperatures (>80° F.) for even relatively short periods of time and warm temperatures (>75° F.) for extended periods of time cause broccoli heads to be rough with uneven flower bud sizes and thus commercially unacceptable. {(Björkman, T., et al. (1998) *High temperature arrest of inflorescence development in broccoli* (*Brassica oleracea var. italica L.*) Journal of Experimental Botany 49:101–106.} As a result of the high sensitivity to heat during growth, broccoli can only be grown in limited areas under cool weather conditions.

Previous attempts at identifying heat tolerant broccoli cultivars have not been successful because broccoli is sensitive to relatively short periods of heat stress thereby making field observations too variable for effective genetic screening. Björkman, et al. (1998).

Thus, there is a need to develop heat tolerant broccoli varieties that will produce commercially acceptable broccoli heads under warm weather heat stress growth conditions. In addition, there is a need to develop heat tolerant broccoli inbred lines useful for producing heat tolerant F1 seed.

SUMMARY OF THE INVENTION

In order to meet these needs, the present invention is directed to heat tolerant broccoli plants. In particular, this invention is directed to broccoli seed capable of germinating and growing into a plant capable of producing a commercially acceptable head under heat stress growth conditions.

The broccoli seed of this invention are capable of germinating into a plant capable of producing a commercially acceptable head under heat stress growth conditions that render the heads of commercially available broccoli commercially unacceptable.

In addition to being heat tolerant, the broccoli seed of this invention are capable of germinating into a plant that is predominately mildew resistant.

The broccoli seed of this invention will produce a plant with a commercially acceptable head when the plant is exposed to a maximum temperature of 90° F. for at least 5 consecutive days during the growth cycle; when the plants are exposed to a maximum temperature of at least 95° F. for at least one day during the growth cycle; when the plants are exposed to a maximum temperature of 85° F. for at least 15 days during the growth cycle; when the plants are exposed to a maximum temperature of at least 75° for at least 25 days during the growth cycle; when the plants are exposed to a maximum temperature of at least 80° C. for at least 20 days during the growth cycle and other heat stress growth conditions.

The broccoli seed of this invention include but are not limited to those seeds designated M7028, M7007, M7009, M7022, 393-2-19, H7008, H7022, 393-2-47, 98-2192, 98-2088, 98-2061, H7007, H7028, H7010, and H7021R. The broccoli seed of this invention further include lines 4243, 4221, 4441, 4274-1, 4274-2, 4278-1, 4284-1, 4285-1, 4354-1, 4354-2, 4377-1, 4318-1, 4320-1, 4320-2, 4321-1, 4437-1, 4476-1, 4462-1, 4308-2, 4309-1, 4355-1, 4412-1, 4301, 4303, 4304, 4317, 4468, 4470, 4471, 4263-1, 4430-1, 4450-1, 4450-2, 4432-1, 4267-1, 7861, 7864, 7865, 7881, 7887, 7935, 8092, 7883, 7914, 7770, 7778.

The broccoli seed of this invention further include lines 4201, 4219, 4237, 4280, 4287, 4288, 4289, 4290, 4291, 4458-1, 4460-1, 4415, 4418, 4395-2.

Each of the lines of this invention can be crossed with other broccoli lines.

The broccoli seeds of this invention include inbred lines, hybrid lines, male lines and female lines, all of which are heat tolerant and capable of producing a commercially acceptable head under heat stress growth conditions.

This invention is further directed to broccoli plants or parts of broccoli plants produced from the broccoli seed of the invention. The invention is further directed to broccoli plants regenerated from tissue culture of the broccoli plants of this invention. The tissue culture of the invention comprises regenerable cells including meristematic tissue, anthers, leaves, ovules, roots, embryos, protoplasts and pollen and plants regenerated from these cells.

The invention is further directed toward transgenic heat tolerant broccoli plants. The transgenic heat tolerant broccoli lines may be resistant to various herbicides or pesticides.

The invention is further directed to broccoli plants having all of the phenotypic characteristics of the plants produced from the heat tolerant broccoli seed of the invention. The invention is further directed to plants resulting from selecting, crossing, breeding or otherwise altering the broccoli plants of this invention.

The invention is further directed to biological material isolated from the plants of this invention. Such material includes but is not limited to RNA, DNA, protein and carbohydrate. The DNA of these plants includes the gene(s) involved in heat tolerance.

This invention is further directed to the seeds and plants produced from crossing other broccoli lines with plants grown from the seed of this invention.

This invention is further directed to methods of breeding heat tolerant broccoli lines.

BRIEF DESCRIPTION OF THE DRAWINGS

The invention will be better understood by reference to the drawings in which.

transverse broad elliptic; (3), transverse elliptic and (4) transverse elliptic narrow.

Figure 1:
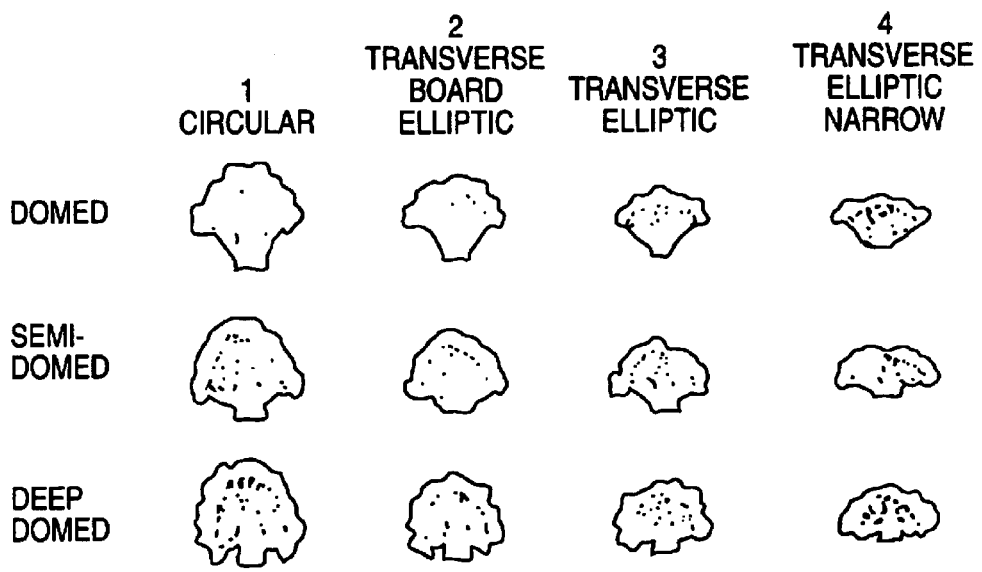
FIG. 1 shows various broccoli head shapes. Broccoli heads are referred to as domed, semi domed and deep-domed. The shapes of the various domes are (1) circular; (2)
Figure 2:
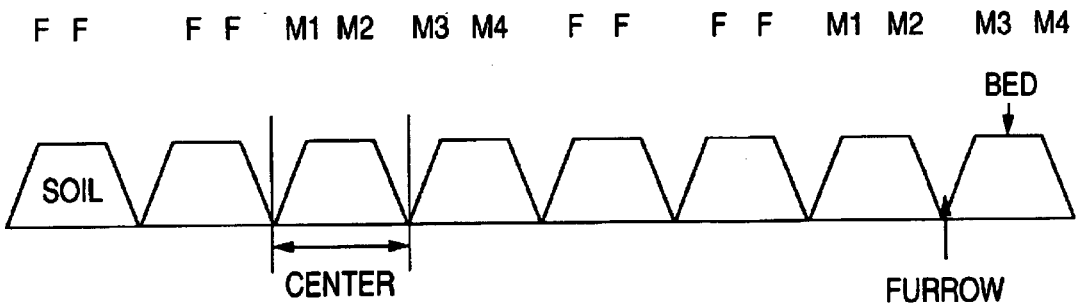

FIG. 2 shows a cross section of eight 40-inch beds utilized for field production of the hybrid seed of this invention. In this diagram: F=female line seed-line; M1=first male planting seed-line; M2=second male planting seed-line; M3=third male planting seed-line and M4=fourth male planting seed-line.

DETAILED DESCRIPTION OF THE INVENTION

In order to more completely understand the invention, the following definitions are provided.

Broccoli: Broccoli (Bressica oleraceaL. var. *italica*) is a cool season vegetable in the mustard family. Principal broccoli varieties currently grown in California include, in the coastal valleys, Everest, Greenbelt, Legacy, Marathon, Ninja, Olympia, Pinnacle, Pirate, Republic, Shogun, and Sultan; in the desert valleys, Arcadia, Captain, Emperor, Everest, Galaxy, Galleon, Greenbelt, Major, Marathon, Ninja, Packman, Patriot, Pirate, and Sultan; and in the San Joaquin Valley, Arcadia, Captain, Everest, Greenbelt, Legacy, Legend, Marathon, Pirate, and Republic. Varieties grown in the Pacific Northwest are: Arcadia, Emerald City, Excelsior, Pakman Patriot, Pirate, Regal, Arcadia, Buccaneer, Emerald City, Emperor, Everest, Excelsior, Green Belt, Green Valiant, Laguna, Legend, Liberty, Major, Marathon, Pakman, Patriot, Pinnacle, Pirate, Premium Crop, Regal, Shogun, Samurai, Triathlon, Windsor, Barbados, Embassy, Green Comet, Green Defender, HMX 1134, Idol. Because, of heat sensitivity, broccoli is typically grown for harvest in the spring and fall.

Commercially Acceptable Broccoli: Commercially acceptable broccoli is broccoli which vegetable growers/shippers find acceptable for sale and consumers find acceptable for personal purchase and, ultimately, human consumption. Commercially acceptable broccoli has small uniform beads, good blue-green to green color, and tight, dome-shaped heads that extend above the leaves for ease of harvest. In commercial plantings under optimum conditions, large leafy broccoli plants produce a compact flower head on a tall, green, branching stalk. The center flower head is from 3 to 8 inches (7.5–20 cm) in diameter and plants average 24 to 36 inches (60–90 cm) tall. Hollow stems, water head rot, brown or yellow beads, bracts (leaflets) within heads, uneven bead size, and excessive branching are undesirable and commercially unacceptable defects in broccoli that can be caused by exposure to heat.

Heat Tolerant Broccoli: Heat tolerant broccoli is broccoli that will produce a commercially acceptable product when grown under heat stress growth conditions for broccoli.

Heat Stress Growth Conditions: Heat stress growth conditions. for broccoli are elevated temperature growth conditions that result in broccoli that exhibit heat stress symptoms that result in a commercially unacceptable product. Heat stress symptoms include non-uniform beads; brown, yellow, light-green or purple colored heads; loose flat heads; prominent leaflets that come through the broccoli head as bracts; hollow stems; water head rot and excessive branching.

Single Plant Selection: Single plant selection is the process of selecting single plants; which exhibit desired traits or characteristics. Seeds from the single plant are collected, stored and then grown in a subsequent growing period for further selections.

Massed: Broccoli plants are massed when a number of plants are selected and brought together for cross-pollination as a group. Massing prevents further inbreeding and tends to "fix" the broccoli line at the stage from which the selections were made.

Self-Pollination/Self-Pollinator: Self-pollination is the process of putting pollen from a plant onto a receptive female flower-part of that same plant. A plant that is a self-pollinator is a plant that accepts its own pollen to make seed that typically will give rise to plants very similar or the same as the self pollinator plant. A plant that is self-pollinated is said to be selfed.

Self-Incompatible: A self-incompatible plant will not, under normal conditions, accept its own pollen nor generate any self-seed. Self-incompatible lines are generally designated "female." Self-incompatible lines are generally crossed with other lines to produce hybrid seed.

Self-Compatible: A self-compatible plant accepts its own pollen and will produce self-seed. Self-compatible lines are generally designated "male."

Progeny: Progeny is a broccoli line that is the offspring of the previous generation broccoli line.

Sessile: Attached to the stem by the base of the leaf.

Petiolate: Attached to the stem via a petiole.

Hybrid: The progeny of cross-fertilization between parents belonging to different genotypes.

Hybrid Vigor: The phenomenon in which the cross of two parent stocks produces hybrids that show increased vigor/heterosis compared to the parent stocks.

Inbred Lines: A nearly homozygous line produced by continuous inbreeding.

Pedigree Bre ding: A system of breeding in which individual plants are selected in the segregating generations from a cross on the basis of their desirability and on the basis of a pedigree record.

The terminology used to describe the broccoli plants of this invention are generally those used by the Plant Variety Protection Office in PVP form STD-470-44 "Objective Description of Variety Broccoli (*Brassica oteracea* var. *italica*)." The following terminology is used herein in comparative study #1 and comparative study #2.

1. REGION OF ADAPTATION (Area where best adapted in USA):
(1) Northwest; (2) NorthCentral; (3) Northeast; (4) Southeast; (5) Southwest; (6) Most regions and (7) Pacific Coast.
2. MATURITY (MainCrop at 50% Harvest):
Harvest Season: (1) Fall; (2) Fall/Winter; (3) Winter/Spring; (4) Spring/Summer; (5) Summer; and (6) Summer/Fall.
Spring Planted: (1) Days from Direct Seeding to 50% Harvest; (2) Days from Transplanting to 50% Harvest; and (3) Length of Harvest Period in days.
Fall Planted: (1) Days from Direct Seeding to 50% Harvest; (2) Days from Transplanting to 50% Harvest; and (3) Length of Harvest Period in days.
Time of beginning of flowering (50% of plants with at least 10% flowers: (1) Early; (2) Med-Early; (3) Medium; (4) Med-Late; and (5) Late.
3. SEEDLING:
Cotyledon Color: (1) Yellow-Green; (2) Light Green; (3) Medium Green; (4) Dark Green; (5) Blue-Green; and (6) Purple-Green.
Cotyledon Anthocyanin: (1) Absent; (2) Weak; (3) Intermediate; and (4) Strong.
Hypocotyl Anthocyanin: (1) Absent; (2) Weak; (3) Intermediate; and (4) Strong.

4. PLANT (At Harvest):
Plant Height; (cm) from soil line to top of leaves
Head Height: (cm) from soil line to top of head
Plant Branches: (1) Few; (2) Medium; and (3) Many.
Plant Habit: (1) Spreading; (2) Intermediate; and (3) Compact.
Market Class: (1) Fresh Market; (2) Processing; and (3) Both
Life Cycle: (1) Annual; (2) Biennial; and (3) Perennial.
Type of Variety: (1) Inbred; (2) Open-Pollinated; and (3) First generation Hybrid.
5. OUTER LEAVES (at Harvest):
Number of Leaves per Plant:
Width at midpoint of plant including petiole:
Length at midpoint of plant including petiole:
Petiole Length:
Leaf Ratio-Length/Width: (1) (2:1); (2) (3:1); (3) (4:1): (4) (5:1); and (5) (6:1).
Leaf Attachment: (1) Sessile; (2) Petiolate; and (3) Sessile and Petiolate (both).
Wax Presence: (1) None; (2) Weak; (3) Intermediate; and (4) Strong.
Foliage Color (with wax if present): 1 Light Green; (2) Medium Green; (3) Dark Green; (4) Grey-Green; (5) Blue-Green; and (6) Purple-Green.
Leaf Shape: (1) Narrow Elliptic; (2) Elliptic; and (3) Broad Elliptic.
Leaf Base: (1) Blunt and (2) Pointed.
Leaf Apex: (1 ) Blunt and (2) Pointed.
Leaf Margins: (1) Straight; (2) Slightly Wavy; and (3) Very Wavy.
Leaf Veins: (1) Thin; (2) Intermediate; and (3) Thick.
Midrib: (1) Not Raised; (2) Slightly Raised; and (3) Raised.
Blistering (1) None; (2) Weak; and (3) Intermediate; and (4) Strong.
Attitude (Leaf Angle from Ground): (1) Horizontal (0–15 degrees); (3) Semi-erect (35–55 degrees); and (5) Erect (80–100 degrees).
Torsion of Leaf Tip: (1) None; (2) Weak; (3) Intermediate; and (4) Strong.
Profile of Upper Side of Leaf: (1) Concave; (2) Planar; and (3) Convex.
6. HEAD (At Market Maturity):
Diameter at widest point:
Depth:
Weight: market trimmed
Color: (1) Light Green; (2) Medium Green; (3) Dark Green; (4) Blue/Green; and (5) Purple.
Head Shape: (1) Circular; (2) Transverse Broad Elliptic; (3) Transverse Elliptic; and (4) Transverse Elliptic Narrow.
Dome Shape: (1) Domed; (2) Semi-domed; and (3) Deep Domed.
Head Size: (1) Small; (2) Medium; and (3) Large.
Compactness: (1) Long Pedicels (Loose); (2) Medium; and (3) Short. Pedicels (Tight).
Surface Knobbling: (1) Fine; (2) Medium; and (3) Coarse.
Beads size: (1) Small; (2) Medium; and (3) Large.
Flower Buds: (1) Even in size; and (2) Uneven in size (cateye).
Anthocyanin Coloration: (1) Absent; 2 Present; (3) Leaf Axils; (4) Leaf Veins; (5) Leaf Blade; (6) Entire Plant; and (7) Leaf Petiole.
Color of Head Leaves: (1) White; (2) Green; (3) Red; and (4) Purple.
Secondary Heads: (1) Completely absent; (2) Basal; (3) Combination; and (4) Axillary along entire main stem up to main head.
Prominence of Secondary Heads: (1) Weak, (2) Intermediate; and (3)=Strong.
Number of Secondary Heads:
7. COLOR:
Flower Color: (1) White; (2) Cream; and (3) Yellow.
Flower Stalk Color: (1) Green; (2) Purple; and (3) Variegated.

8. DISEASE RESISTANCES:
1 = Most Susceptible
5 = Intermediate
9 = Most Resistant

| | |
|---|---|
| Black Leg (*Leptosphaeria maculans*) | Black Leg |
| Black Spot (Alternaria spp.) | Black Spot |
| Black Rot | Black Rot |
| Bottom Rot (*Rhizoctonia solani*) | Bottom Rot |
| Cauliflower Mosaic Virus | Cauliflower Mosaic Virus |
| Cerospora Leaf Spot (*Cercospora brassicicola*) | Cerospora Leaf Spot |
| Clubroot (*Plasmodiophora brassicae*) | Clubroot |
| Downy Mildew (*Peronospora parasitica*) | Downy Mildew |
| Erwinia Sp. | Erwinia Sp. |
| Phytophthora Root Rot (*Phytophthora megasperma*) | Phytophthora Root Rot |
| Powdery Mildew (*Erysiphe polygoni*) | Powdery Mildew |
| Pseudomonas | Pseudomonas |
| Ring Spot (*Mycosphaerella brassicicola*) | Ring Spot |
| Turnip Yellow Mosaic Virus | Turnip Yellow Mosaic Virus |
| Verticillium wilt (*Verticillium albo-atrum*) | Verticillium wilt |
| White Blister (*Albugo candida*) | White Blister |
| Xanthomonas campetis | Xanthomonas campetis |
| Yellows (*Fusarium oxysporum*) | Yellows |

9. OTHER RESISTANCE:
1=Most susceptible
5=Intermediate
9=Most Resistant
Insect
Buttoning
Blindness
Bolting
Brown beads
Drought
Cold
Hollow Stem
Riceyness
Whiptail
10. HEAT TOLERANCE:

Heat tolerance was measured on a scale of 1–9 with 9 being the most heat tolerant and 1 being the least heat tolerant. For heat tolerance, ratings of five (5) or below are indicative of a broccoli plant that produced a commercially unacceptable head. A rating of six (6) is indicative of broccoli plants that exhibit no heat stress symptoms when exposed to 90° F. A rating of seven (7) is indicative of broccoli plants that exhibit no heat stress symptoms when exposed to 95° F. A rating of eight (8) is indicative of broccoli plants that exhibit no heat stress symptoms when exposed to 100° F. A rating of nine (9) is indicative of broccoli plants that exhibit no heat stress symptoms when exposed to 105° F. In some studies, plants were not exposed to a temperature of 105° F. so that a rating of 9.0 could not be assigned.

Under some circumstances, the heat tolerant ratings are followed by a (+) or (−) to indicate a plant exhibiting symptoms slightly better (+) or slightly worse (−) than the assigned number. In other circumstances, the ratings are presented as a friction of a rating number. For example, a rating of 7.1 is slightly better than a rating of 7.0. A rating of 7.5 is half way between a rating of 7.0 and 8.0. A rating of 6.8 is slightly worse than a rating of 7.0. A slightly higher rating means that the heat stress symptoms were slightly less evident. Similarly, a slightly lower rating means that the heat stress symptoms were less evident.

Taking into account these definitions, the present invention is directed to heat tolerant broccoli plants. The heat tolerant broccoli of this invention is capable of producing a commercially acceptable product when grown under heat stress conditions.

Heat stress is exhibited in broccoli by a number of different symptoms. These symptoms include non-uniform beads; brown, yellow, light-green or purple colored heads; flat heads; bracts (leaflets in the head); rapid fracturing of the head, which reduces the harvest period; "cateye" (death of growing points), extremely small heads, and hollow stems.

Each of these symptoms is generally viewed as commercially unacceptable. The greater the number of heat stress symptoms, the more commercially unacceptable the broccoli plant. Heat stress symptoms in broccoli result from a number of interacting factors. The most important of these interacting factors are the temperature, the duration of the high temperature exposure (hours, days, weeks), the available soil moisture supply and the wind speed. Of critical importance is the timing of the exposure to the heat stress conditions during the growth cycle of broccoli. It has been shown that heat stress of broccoli can be due to an inhibition of the enlargement of broccoli bud primordia. Broccoli buds are not as sensitive to heat once they differentiate. The different heat sensitivity and resulting contrast between the delayed buds and the unaffected buds causes the uneven head appearance under heat stress growth conditions. If heat stress occurs prior to bud development (i.e., during vegetative development) no injury is generally seen. If the heat stress is applied late in bud development, many buds are affected but these buds can be obscured by the older buds.

Because of extreme sensitivity to heat stress, broccoli grown in the spring and the fall, when cooler temperatures are the norm, are at less risk of heat stress. However, a single day during the spring or fall with a high temperature of 100° F. or several (2–3) warmer days (>80° F.) or multiple (5–7) warm days (>75° F.) at the critical point during broccoli bud development can render an entire field so damaged by heat stress that none of the heads are commercially acceptable.

The present invention is thus directed toward the development of heat tolerant broccoli varieties and hybrids. The broccoli varieties and hybrids of this invention will produce commercially acceptable heads when the plant are grown during heat stress growth conditions during late spring, summer, and early fall in California, Arizona, Mexico, and many other areas traditionally considered to be too warm for broccoli growth, or at risk of heat stress.

Broccoli Production

Broccoli may be grown by transplant production or by direct seeding. For transplant production, plants may be started in hotbeds or greenhouses. Broccoli seedlings grown in a hotbed need a loose, easily pulverized loam that is not too fertile. If the plants are started in hotbeds, soil fumigation is needed to control weeds, soil borne diseases, and insects. Seeds are planted one-quarter to one-half inch deep in rows 4 to 6 inches apart with 2 to 4 seeds per inch and covered with a sash or plastic covering. The seedlings are thinned at the two-leaf stage allowing 1½ inches between plants. Plants are watered twice daily and fertilized with soluble fertilizer at least every 2 weeks. Proper ventilation is important and can be maintained by raising the sash or plastic covering during the hottest portion of the day. In the hotbed, if properly handled, 3 or 4 ounces of seed will produce enough seedlings to plant 1 acre. When seed is planted in beds, it generally requires about 6 to 8 weeks from seed to plants for the spring crop, and about 4 to 5 weeks for the fall crop.

In the greenhouse, a variety of plant growing containers may be used (i.e. plastic cell packs, peat pots, and speedling trays) for growing broccoli. These containers can be filled with an artificial media, usually a combination of peat, perlite, vermiculite, and in some instances bark. The seeds can be sown directly into the containers and thinned upon emergence to 1 plant per cell or pot. In the greenhouse, it generally requires 5 to 6 weeks from seed to plants for the spring crop and 4 to 5 weeks for the fall crop.

For direct seeding, broccoli seeds may be direct seeded in the field using a precision planter. Seed required for one acre is generally 0.75 to 1.25 pound when using a precision seeder.

Origin and Parentage of Heat Tolerant Broccoli Plants

The broccoli of this invention were created by classical plant breeding as well as anther culture techniques. The breeding history of the "inbred," "self compatible" and "male" lines identified are exemplified by the following breeding histories.

A. Development of Inbred Lines

Numerous heat tolerant inbred lines were developed. For illustrative, but nonlimiting purposes, the breeding histories of the following inbred lines are presented. Unless otherwise noted, single plant selections were made each year for plants exhibiting heat tolerance.

1. Inbred Lines 393-2-19, 393-2-47, and 393-2-32

All lines designated "393-2-XX" where XX represents a different number for a line were isolated and developed as indicated below. Representative lines include 393-2-19, 393-2-47, 393-2-32.

Fall, Year 1 Commercial broccoli hybrid Marathon was crossed with broccoli hybrid "No. 608" obtained from IM Foods, Incorporated, Gilroy, Calif.

Summer, Year 2 F1 seed from Marathon×No. 008 were planted into row number 393 of a summer broccoli trial in Gilroy, Calif., and single plant selections were made for heat tolerance and downy mildew resistance.

Fall, Year 2 Single plant selection number 2 from row 393, i.e. "393-2", which had exhibited good heat tolerance and downy mildew resistance, was entered into anther culture.

Spring, Year 3 Anther culture product numbers 19 and 47 from 393-2, i.e. "393-2-19," "393-2-47" and "393-2-32" were transplanted into the greenhouse in Gilroy, Calif. 393-2-19, 393-2-47 and 393-2-32 were observed to exhibit desirable horticultural traits for deep dome-shaped head, lack of side shoots, good vigor, and high yield. 393-2-19, 393-2-47 and 393-2-32 also demonstrated ability to produce self-pollinated seed.

Summer, Year 4 The original seed from 393-2-19, 393-2-47 and 393-2-32 made in the greenhouse in Spring, year 3, were seeded in the greenhouse in Summer, year 4, and subsequently transplanted to the field for evaluation in Gilroy, Calif., in the summer. 393-2-19 and 393-2-47 exhibited outstanding uniformity and were considered breeding true as a spontaneously doubled-haploid, "inbred", line. Plants were taken from the field plot for self-pollination and subsequent seed increase.

From Year 5 to Present 393-2-19, 393-2-47 and 393-2-32 have consistently exhibited exceptionally good uniformity and stability through generations of seed increase with no variants or off types plants ever observed.

In the breeding history described above, commercial broccoli hybrid Marathon was crossed with broccoli hybrid No. 608 obtained from IM Foods, Incorporated, Gilroy, Calif. The commercially available broccoli hybrid Marathon was selected for the initial cross because it had demonstrated good yield potential. Hybrid No. 608 was selected for the initial cross because it was thought to have less side shoots, an advantageous characteristic for harvesting.

During the breeding process, F1 seed from Marathon×No. 608 were planted and grown. Selections were made for heat tolerance and downy mildew resistance. The heat tolerance selection was conducted at head formation through harvest maturity. The selection criteria were smooth domed head, even flower-bud size, good head color, lack of bracting (leaflets in the head), and an ability to hold a good head shape through harvest maturity. The downy mildew selection was conducted throughout the growth cycle of the plants. The selection for downy mildew resistance was based on plants with no mildew lesions or a greatly reduced number of lesions present on any leaves as compared to non-resistant plants.

Multiple single plant selections exhibiting heat tolerance and downy mildew resistance were entered into anther culture. Anther culture procedures are well known in the art of plant breeding. In anther culture techniques, the undifferentiated pollen mother cells that exist in immature broccoli anthers are stimulated in vitro into embryonic states by procedures well known in the literature. The undifferentiated pollen mother cells may be subjected to treatments of higher temperatures, light and dark and specialized media growth conditions including hormone simulation. Plant growth conditions of 60° F. and bright light followed by a heat shock of 90° F. after anther excision and culturing can help stimulate embryogenisis. This process can stimulate the development of embryonic growth wherein the haploid (one-half the chromosome number) pollen mother cell multiplies and grows into callus tissue. The callus tissue, through the use of specialized media, hormone treatments, and controlled temperature and light can be stimulated to make green plant shoots and eventually functional roots. Some of these haploids spontaneously double their chromosome number, thus; generating "di-haploids," which are essentially completely homozygous. These highly homozygous lines are genetically equivalent to the end result of many years of self-pollination by conventional means.

In a preferred format, anther cultures are prepared as described in Keller, et al., Embryogenesis and Plant Regeneration in *Brassica napus* Anther Cultures, *Canadian Journal of Botany* 55: 1383–1388 (1977); Keller, et al. Production of Haploids via Anther Culture in *Brassica Oleracea* Var. *Italica, Euphytica* 32: 151–159 (1983); and Orton, et al., Segregation of Genetic Markers among Plants Regenerated From Cultured Anthers of Broccoli (*Brassica oleracea* var. '*italica*') *Theor Appl Genet* 69:637–643 (1985).

In one format, broccoli anthers are prepared and cultured as follows. Immature broccoli racemes are removed from broccoli heads as they begin to elongate, but before the first buds are opened. Racemes are then sterilized, for example in 20% W:V household bleach for 15 minutes under agitation with one drop of detergent per 100 ml as a surfactant. The racemes are then washed at least three times with sterile distilled water for generally 10 minutes per wash. Anthers are then generally removed by carefully peeling back the immature calyx and corolla and gently rupturing the point of filament attached to the anther axis. Care must be taken to minimize damage to the anther culture. Anthers are then placed into liquid culture medium as described in Keller, et al. (1977). Such culture medium may include L-serine at a concentration of 100 mg/l. Anthers are cultured at, for example, 35° C. for 36 h and transferred to 25° (all in the dark). In some circumstances, anther-derived embryos are then kept in continuous fluorescent light (25° C.) for 1 week to permit greening and then transferred to hormone-free solidified $B_5$ medium as described by Gamborg, et al. *Exp. Cell Res.* 50: 151–158 (1968). Upon transfer to the hormone-free medium, the anther-derived embryos are cultured at 25° C. in light. Embryos which fail to develop into plantlets may be cut into sections and cultured on a modified Murashige and Skoog medium [Murashige, et al., *Physiol. Plant* 15: 473–497 (1962)] containing 0.8% agar, 2% sucrose, $5 \times 10^{-6}$ M benzyladenine and $10^{-7}$ M napthaleneacetic acid (NAA) to induce shoot regeneration. To induce rooting, developing shoots are excised and cultured on $B_5$ medium in, for example, 60 ml sterilin bottles. Rooted plantlets may then be planted in Jiffy-7 peat pellets and kept moist in a mist chamber. After 2 weeks, the broccoli plants can then be transferred to soil and grown in the greenhouse for further selections.

Once transferred to the greenhouse, various plants were selected based on desired phenotypical characteristics including an ability to produce self-pollinated seed. Self-pollination is advantageous because it permits seed increase and bulking of seed without random cross-pollination.

2. Inbred Lines: 4243, 4221 and 4441

Using the procedures generally outlined above for 393-2-19 and 393-2-47, inbred lines 4243, 4221 and 4441 were isolated following the pedigree chart outlined below. IM Foods 608, Cruiser, Marathon and Sprinter are commercially available lines. Unless otherwise noted, all selections were single plant selections for heat tolerance. 393-2-19 is the same inbred line described above. Each season, the single plant selection exhibiting heat tolerance were selfed and seed was harvested for the next growing season.

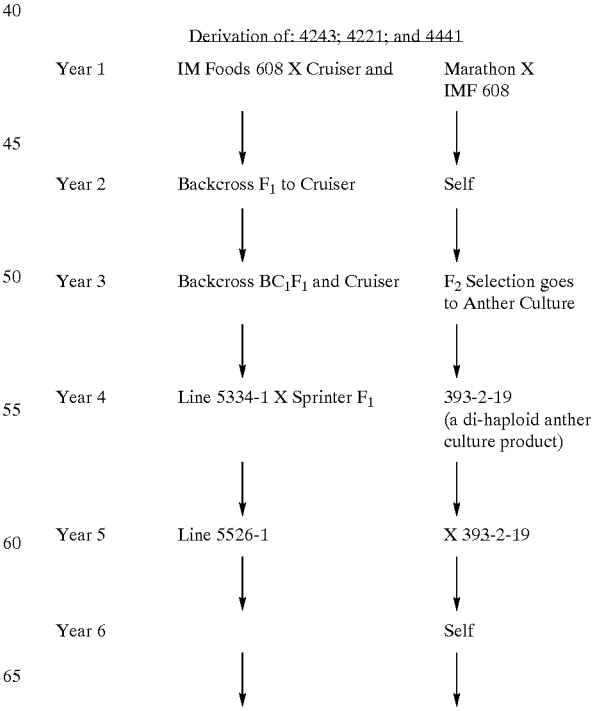

3. Inbred Lines: 4274-1; 4274-2; 4278-1; 4284-1; 4285-1; 4354-1; 4354-2; 4377-1

Inbred lines 4274-1; 4274-2; 4278-1; 4284-1; 4285-1; 4354-1; 4354-2; 4377-1 were isolated following the pedigree chart outlined below using the procedures generally described above for inbred lines 393-2-19 and 393-2-47. Unless otherwise noted, single plant selections were made for heat tolerance.

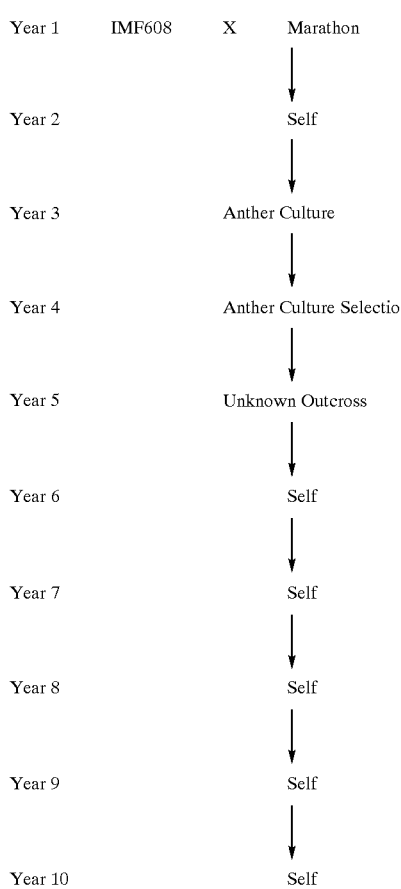

Derivation of: 4274-1; 4274-2; 4278-1; 4284-1; 4285-1; 4354-1; 4354-2; 4377-1

| Year 1 | IMF608 | X | Marathon |
| Year 2 | | | Self |
| Year 3 | | | Anther Culture |
| Year 4 | | | Anther Culture Selection 393-2-47 |
| Year 5 | | | Unknown Outcross |
| Year 6 | | | Self |
| Year 7 | | | Self |
| Year 8 | | | Self |
| Year 9 | | | Self |
| Year 10 | | | Self |

4. Inbred Lines: 4318-1; 4320-1 and 4320-2; 4321-1; 4437-1; 4476-1; 4462-1

Inbred lines 4318-1; 4320-1 and 4320-2; 4321-1; 4437-1; 4476-1; 4462-1 were isolated following the pedigree chart outlined below using the procedures generally outlined above for inbred lines 393-2-19 and 393-2-47. Commercially available line Marathon was selfed. Repeated single plant selections for heat tolerance were made to produce the resulting lines. In year 6, the selected line was mass pollinated.

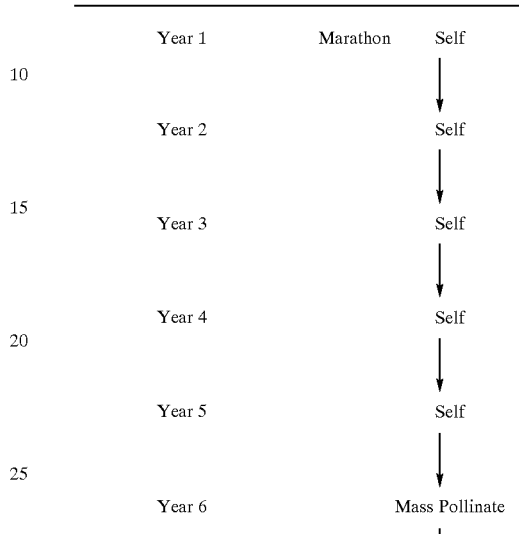

Derivation of: 4318-1; 4320-1 and 4320-2; 4321-1; 4437-1; 4476-1; 4462-1

| Year 1 | Marathon | Self |
| Year 2 | | Self |
| Year 3 | | Self |
| Year 4 | | Self |
| Year 5 | | Self |
| Year 6 | | Mass Pollinate |
| Year 7 | | Self |

5. Inbred Lines: 4308-2; 4309-1; 4355-1; 4412-1; 4301; 4303; 4304; 4317; 4468; 4470; 4471

Inbred lines 4308-2; 4309-1; 4355-1; 4412-1; 4301; 4303; 4304; 4317; 4468; 4470; 4471 were isolated following the pedigree chart outlined below using the techniques generally outlined above for inbred lines 393-2-19 and 393-2-47. In year 9, the selected lines were brush pollinated, i.e., pollinated with a brush. Single plant selections were made for heat tolerance.

Derivation of: 4308-2; 4309-1; 4355-1; 4412-1; 4301; 4303; 4304; 4317; 4468; 4470; 4471

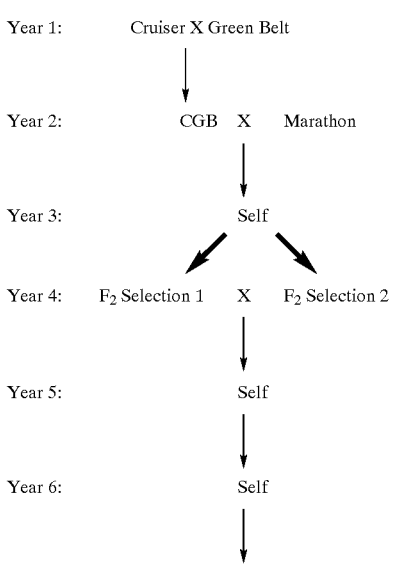

| Year 1: | Cruiser X Green Belt |
| Year 2: | CGB X Marathon |
| Year 3: | Self |
| Year 4: | F₂ Selection 1 X F₂ Selection 2 |
| Year 5: | Self |
| Year 6: | Self |

-continued

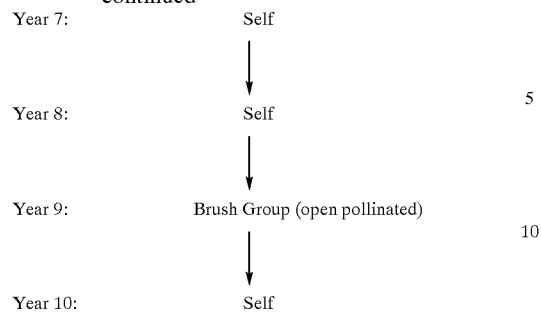

6. Inbred Lines 4263-1; 4430-1; 4450-1 and 4450-2

Inbred lines 4263-1; 4430-1; 4450-1 and 4450-2 were isolated following the pedigree chart outlined below using the techniques generally outlined above for inbred lines 393-2-19 and 393-2-47. Single plant selections were made for heat tolerance.

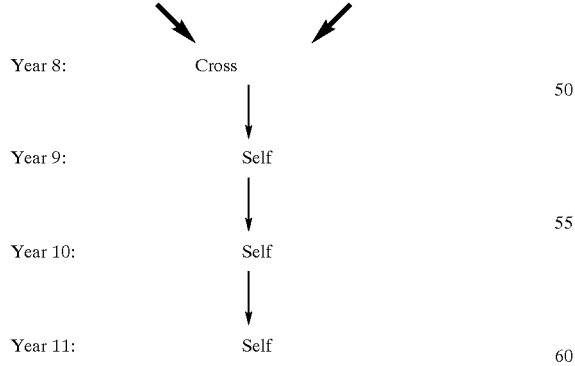

7. Inbred Line 4432-1

Inbred line 4432-1 was isolated following the pedigree chart outlined below using the techniques generally outlined above for inbred lines 393-2-19 and 393-2-47. Single plant selections for heat tolerance were made.

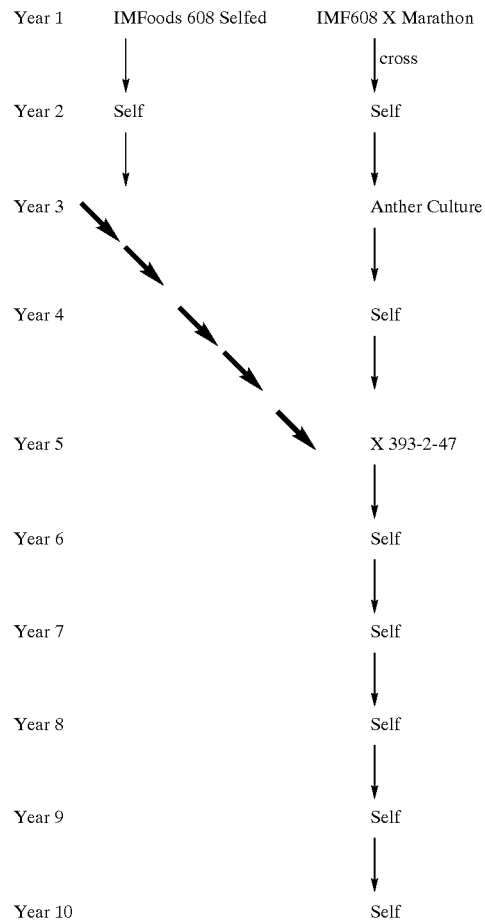

8. Inbred Line 4267-1 (="2192")

Inbred line 4267-1 (="2192") was isolated following the pedigree chart outlined below using the techniques generally outlined above for inbred line 393-2-19. Single plant selections were made for heat tolerance.

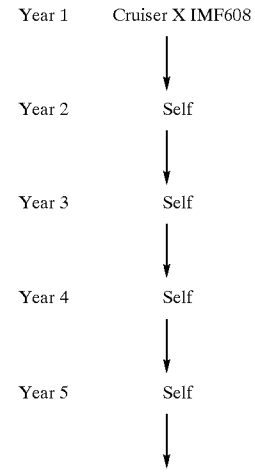

-continued

| Year 6 | Self |
| Year 7 | Open-pollinate |

9. Inbr d Line 7861

Inbred line 7861 was isolated following the pedigree chart outlined below using the techniques generally outlined for inbred lines 393-2-19 and 393-2-47 outlined above. Single plant selections were made for heat tolerance.

Derivation of: 7861

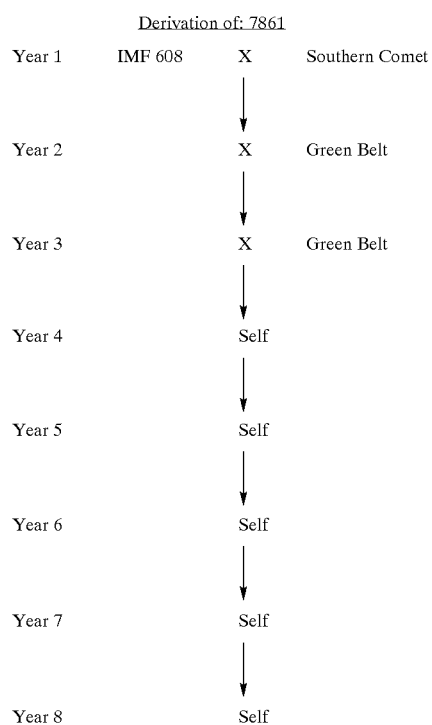

| Year 1 | IMF 608 | X | Southern Comet |
| Year 2 | | X | Green Belt |
| Year 3 | | X | Green Belt |
| Year 4 | | Self | |
| Year 5 | | Self | |
| Year 6 | | Self | |
| Year 7 | | Self | |
| Year 8 | | Self | |

10. Inbred Line 7864

Inbred line 7864 was isolated following the pedigree chart outlined below using the techniques generally outlined for inbred lines 393-2-19 and 393-2-47 outlined above. Single plant selections were made for heat tolerance.

Derivation of: 7864

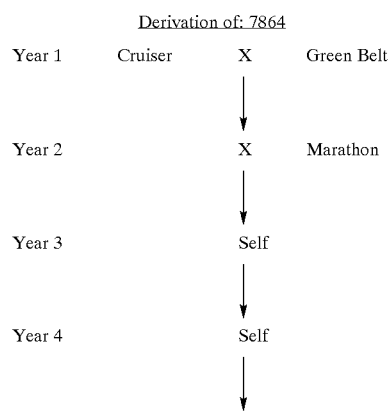

| Year 1 | Cruiser | X | Green Belt |
| Year 2 | | X | Marathon |
| Year 3 | | Self | |
| Year 4 | | Self | |

-continued

| Year 5 | Self |
| Year 6 | Self |
| Year 7 | Self |
| Year 8 | Self |

11. Inbred Line 7865

Inbred line 7865 was isolated following the pedigree chart outlined below using the techniques generally outlined for inbred lines 393-2-19 and 393-2-47 outlined above. Single plant selections were made for heat tolerance.

Derivation of: 7865

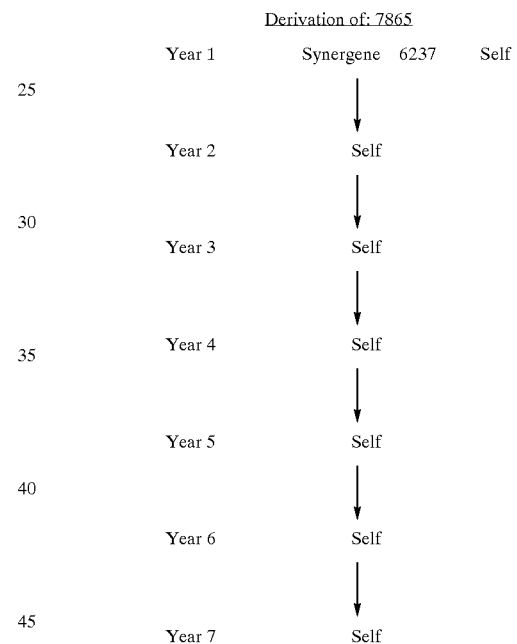

| Year 1 | Synergene | 6237 | Self |
| Year 2 | | Self | |
| Year 3 | | Self | |
| Year 4 | | Self | |
| Year 5 | | Self | |
| Year 6 | | Self | |
| Year 7 | | Self | |

12. Inbred Lin 7881 and 1551

Inbred lines 7881 and 1551 were isolated following the pedigree chart outlined below using the techniques generally outlined for inbred lines 393-2-19 and 393-2-47 outlined above. Single plant selections were made for heat tolerance.

Derivation of: 7881 and 1551

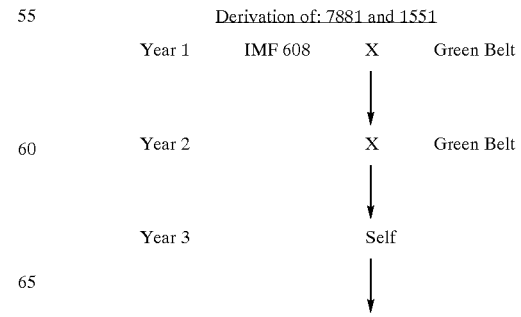

| Year 1 | IMF 608 | X | Green Belt |
| Year 2 | | X | Green Belt |
| Year 3 | | Self | |

13. Inbred Line 7887

Inbred line 7887 was isolated following the pedigree chart outlined below using the techniques generally outlined for inbred lines 393-2-19 and 393-2-47 outlined above. Single plant selections were made for heat tolerance.

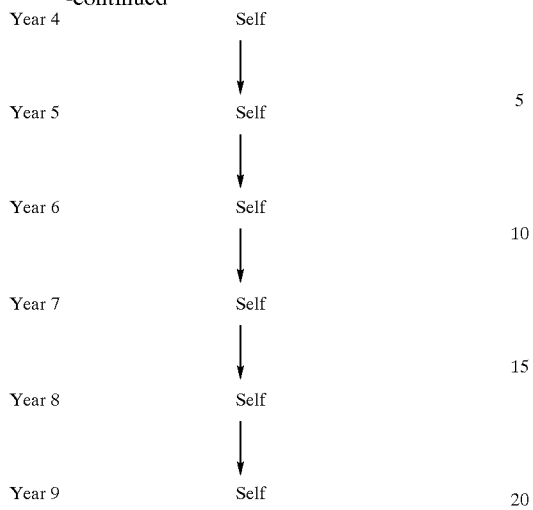

Derivation of: 7887
- Year 1: IMF 608 Self
- Year 2: X Cruiser
- Year 3: Self
- Year 4: Self
- Year 5: Self
- Year 6: Self
- Year 7: Self
- Year 8: Self
- Year 9: Self

14. Inbred Line 7935

Inbred line 7935 was isolated following the pedigree chart outlined below using the techniques generally outlined for inbred lines 393-2-19 and 393-2-47 outlined above. Single plant selections were made for heat tolerance.

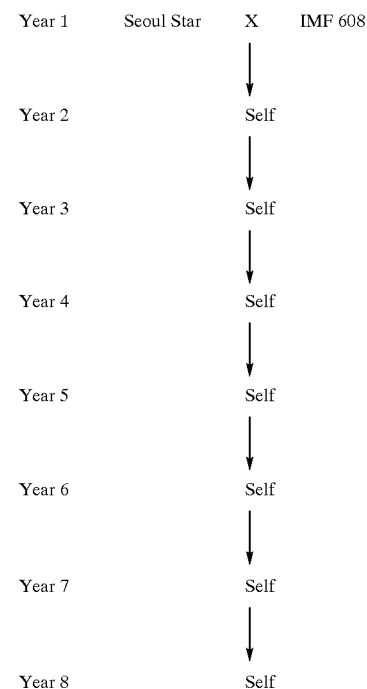

Derivation of: 7935
- Year 1: Seoul Star X IMF 608
- Year 2: Self
- Year 3: Self
- Year 4: Self
- Year 5: Self
- Year 6: Self
- Year 7: Self
- Year 8: Self

15. Inbred Line 8092

Inbred line 8092 was isolated following the pedigree chart outlined below using the techniques generally outlined for inbred lines 393-2-19 and 393-2-47 outlined above. Single plant selections were made for heat tolerance.

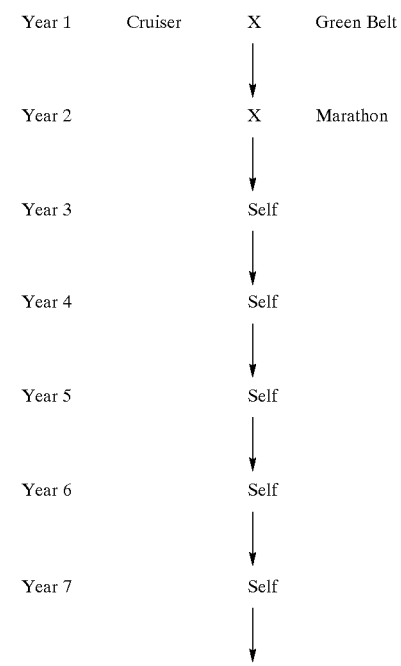

Derivation of: 8092
- Year 1: Cruiser X Green Belt
- Year 2: X Marathon
- Year 3: Self
- Year 4: Self
- Year 5: Self
- Year 6: Self
- Year 7: Self -continued

| Year 8 | Self |
| Year 9 | Self |

16. Inbred Line 7883

Inbred line 7883 was isolated following the pedigree chart outlined below using the techniques generally outlined for inbred lines 393-2-19 and 393-2-47 outlined above. Single plant selections were made for heat tolerance.

Derivation of: 7883

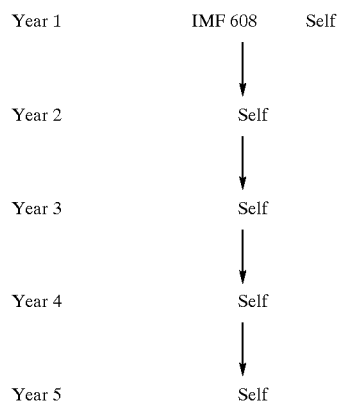

| Year 1 | IMF 608 | Self |
| Year 2 | Self | |
| Year 3 | Self | |
| Year 4 | Self | |
| Year 5 | Self | |

17. Inbred Line 7914

Inbred line 7914 was isolated following the pedigree chart outlined below using the techniques generally outlined for inbred lines 393-2-19 and 393-2-47 outlined above. Single plant selections were made for heat tolerance.

Derivation of: 7914

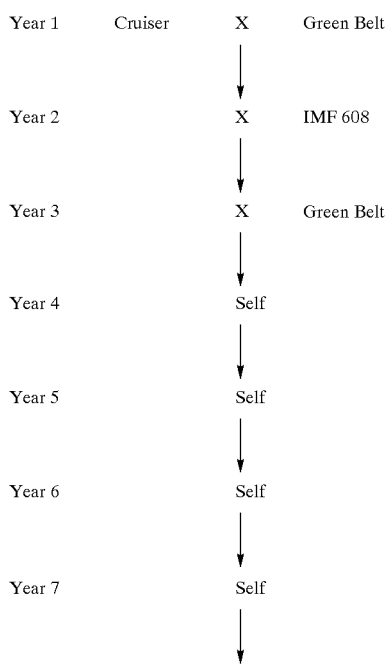

| Year 1 | Cruiser | X | Green Belt |
| Year 2 | | X | IMF 608 |
| Year 3 | | X | Green Belt |
| Year 4 | | Self | |
| Year 5 | | Self | |
| Year 6 | | Self | |
| Year 7 | | Self | |

-continued

| Year 8 | Self |
| Year 9 | Self |

18. Inbred Lines 7770 and 5580-2

Inbred lines 7770 and 5580-2 were isolated following the pedigree chart outlined below using the techniques generally outlined for inbred lines 393-2-19 and 393-2-47 outlined above. Single plant selections were made for heat tolerance.

Derivation of: 7770 and 5580-2

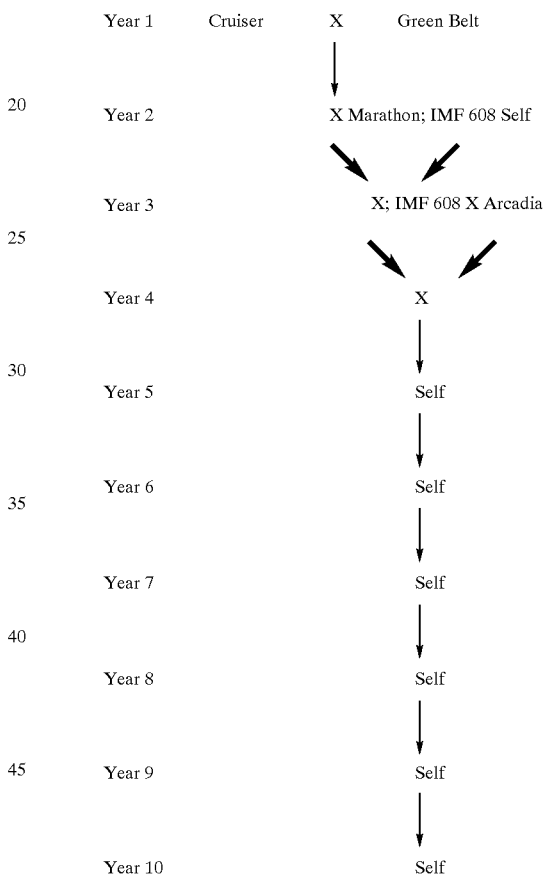

| Year 1 | Cruiser | X | Green Belt |
| Year 2 | | X Marathon; IMF 608 Self | |
| Year 3 | | X; IMF 608 X Arcadia | |
| Year 4 | | X | |
| Year 5 | | Self | |
| Year 6 | | Self | |
| Year 7 | | Self | |
| Year 8 | | Self | |
| Year 9 | | Self | |
| Year 10 | | Self | |

19. Inbred Line 7778

Inbred line 7778 was isolated following the pedigree chart outlined below using the techniques generally outlined for inbred lines 393-2-19 and 393-2-47 outlined above. Single plant selections were made for heat tolerance.

Derivation of: 7778

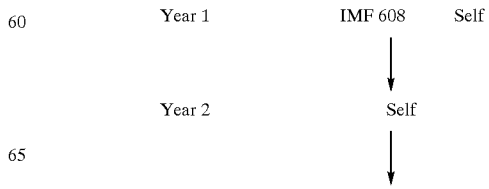

| Year 1 | IMF 608 | Self |
| Year 2 | Self | |

-continued

| Year 3 | Self |
| Year 4 | Self |
| Year 5 | Self |
| Year 6 | Self |
| Year 7 | Self |
| Year 8 | Self |

B. Self Incompatible Lines

Numerous heat tolerant self-incompatible ("female") lines were developed. For illustrative, but not limiting purposes, the breeding histories of the following self-incompatible lines are presented. Unless otherwise noted, single plant selections were made for heat tolerance.

1. Self-incompatible Lines: 4201; 4219, 4237, 4280, 4287, 4288, 4289, 4290, 4291, 4458-1, 4460-1

Broccoli lines 4201; 4219, 4237, 4280, 4287, 4288, 4289, 4290, 4291, 4458-1, 4460-1 were isolated following the pedigree chart outlined below using the procedures generally outlined above for the isolation of 393-2-19.

Derivation of: 4201; 4219, 4237, 4280, 4287, 4288, 4289, 4290, 4291, 4458-1, 4460-1

| Year 1 | IMF608 X Marathon |
| Year 2 | Self |
| Year 3 | Anther Culture |
| Year 4 | 393-2-19     393-2-47 |
| Year 5 | Self     Self |
| Year 6 | X (Cross) |
| Year 7 | Self |
| Year 8 | Self |

-continued

| Year 9 | Self |
| Year 10 | Self |

2. Self Incompatible Line: 4415

Broccoli line 4415 was isolated following the pedigree chart outlined below using the procedures generally outlined above for 393-2-19.

Derivation of: 4415

| Year 1 | IMF608 X Green Belt |
| Year 2 | X Green Belt |
| Year 3 | Self |
| Year 4 | Self |
| Year 5 | Self |
| Year 6 | Self |
| Year 7 | Self |
| Year 8 | Self |
| Year 9 | Self |
| Year 10 | Open-pollinate |

3. Self Incompatible Line: 4418

Broccoli line 4418 was isolated following the pedigree chart outlined below using the procedures outlined above for 393-2-19.

Derivation of: 4418

| Year 1 | Green Belt X Cruiser |
| Year 2 | X Marathon     Shogun X IMF608 |
| Year 3 | Cross |

-continued

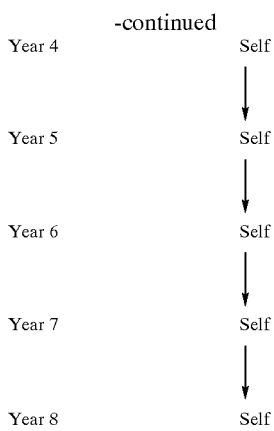

4. Self Incompatible Line 4395-2

Broccoli line 4395-2 was isolated following the pedigree chart outlined below using the procedures generally outlined above for 4935-2.

Derivation of: 4395-2

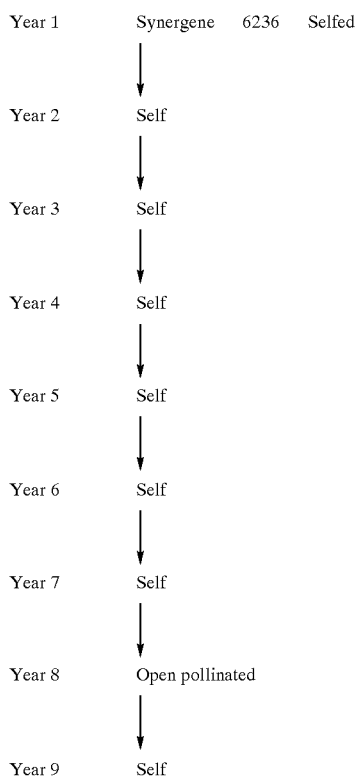

C. Male Lines

Numerous heat tolerant "male" broccoli lines have been identified and shown stable and uniform. For illustrative but non-limiting purposes, the breeding histories of the M7007, M7009 and M7028 are provided as follows.

The "Cruiser" broccoli line was selected for initial crosses because it was a commercially available hybrid that showed a small degree of heat tolerance which was rated at approximately 5 and also had a nicely elevated head.

M7007

Year One IM Hybrid No. 608 obtained from IM Foods, Incorporated, Gilroy, Calif., was self-pollinated.

Year Two F2 of Hybrid No. 608 is crossed with Cruiser, which was obtained from Royal Sluis, a Dutch seed company.

Year Three Heat tolerant single plant selection of the F2 Hybrid 608/Cruiser with heat tolerance equaling 8− was made.

Year Dour Heat tolerance equaling 7+single plant selection gives [(No. 608) F2/Cruiser] F3.

Year Five Eight selections are selfed and massed selected to give [(No. 608) F2/Cruiser] F4.

Year Six Twelve selections are massed.

Year Seven Fifteen selections are massed.

Year Eight Five selections are massed selected and entered into a large isolation cage increase to give the finished line M7007.

M7009

Year One IM Hybrid No. 608 is self-pollinated.

Year Two F2 of Hybrid No. 608 is crossed with Cruiser.

Year Three Heat tolerant single plant selection of the F2 Hybrid 608/Cruiser with heat tolerance equaling 8− was made.

Year Four Heat tolerance equaling 7+single plant selection gives [(No. 608) F2/Cruiser] F3.

Year Five Eight selections are selfed and massed to give [(No. 608) F2/Cruiser] F4.

Year Six Twelve selections are massed.

Year Seven Fifteen selections are massed.

Year Eight Five selections are massed selected and entered into a large isolation cage increase to give the finished line.

Year Nine Seed storage.

Year Ten Six selections are massed selected and entered into a large isolation cage increase to give finish line M7009.

M7028

Year Two F2 of Hybrid No. 608 is crossed with Cruiser.

Year Three Heat tolerant single plant selection of the F2 Hybrid 608/Cruiser with heat tolerance equaling 8− was made.

Year Four Made single plant selection. [(No. 608) F2/Cruiser] F3

Year Five Made single plant selection with heat tolerance equaling 7. [(No. 608) F2/Cruiser] F4

Year Six Made single plant selection with heat tolerance equaling 7. [(No. 608) F2/Cruiser] F5

Year Seven Selected five plants, massed selected and entered into a large isolation cage to give finished line M7028.

The male lines of this invention can be crossed with female lines (self-incompatible) to produce hybrid seed. The female lines may or may not be heat tolerant. Encompassed within the scope of this invention are the hybrid seed produced from crossing the male lines of this invention with other broccoli lines of interest. Hybrid seed includes but is not limited to H7007, H7008, H7028.

Hybrid Seed Production

For hybrid seed production of heat tolerant broccoli seed, two lines are selected for production. The lines are designated male or female, with the female being the recipient of the male line pollen. Either the male or female or both lines may be heat tolerant as defined by this invention. Broccoli plants flower with both the female and male parts and are capable of self-pollination. The line designated "female" is generally "self-incompatible," which means it will not accept its own pollen, a process developed in the plant by breeding. The line designated "male" is generally "self-compatible" and will accept its own pollen. Since self-incompatible lines will not accept their own pollen, but will out-cross with other broccoli pollen. Self-incompatible lines produce the commercially desired hybrid seed. The male line is the pollen provider to the female line. The cross of the self-compatible male line and the self-incompatible female line will produce a seed that is a hybrid.

Once a hybrid has been selected for seed production, a "nick" study is done. The nick study identifies the flowering period of the female, i.e. when it will start to flower and for how long it will flower. A nick study is also done for the male line and the two are compared. The nick study gives the data needed to determine if the female will require 1, 2, 3, or 4 male planting dates to cover its full flowering period.

Once the data from the nick study is obtained, seed of the female and the first male are planted in the greenhouse. The second male is planted in the greenhouse 7–10 days later, with the third male planted another 7–10 days after that, and the final or $4^{th}$ male: planted within 10 more days. The female is seeded in the greenhouse at approximately 11,000 plants for each production acre and each male planting at 7,000 plants. Forty-five days from being planted in the greenhouse the female and first male are ready for transplanting in the field. The three remaining males are each transplanted into the field within 45 days of their individual greenhouse planting dates.

Field Production of Hybrid Seed

Field production of the hybrid seed is begun when all of the female plants and the first male plants from the greenhouse are transplanted into the field. Transplanting can be done by machine or by hand with large crews. The plants are placed into the soil on prepared listed beds that are on 40-inch centers (see FIG. 2). The depth of the planting is generally 3 inches, but depends on the size of the transplant plug. Each plant is separated approximately eighteen inches apart going down the seed-line and each parallel seed-line on a single bed is twelve inches apart. The successive plantings of the second, third, and fourth male follow the female planting at approximately ten day intervals. An illustrative planting schedule is as follows.

October 15 female transplanting date

October 15 first male transplanting date

October 25 second male transplanting date

November 4 third male transplanting date

November 14 fourth male transplanting date

The dates are not fixed, but are an approximation for illustrative and non-limiting purposes.

Once all the plantings are accomplished, the field is watched for typical cultural problems found in all broccoli production, whether for seed or vegetable. These problems include weeds, diseases, insect pests, irrigation, fertilization, and cultivation.

The singular difference for a seed production field as compared to a broccoli production field is the use of rogueing. Rogueing is simply the walking through and examination of a field and checking each plant for correctness to type. Any plant that does not fit the proper description for type is pulled and destroyed or "rogued." The rogueing starts within thirty days of the last male transplanted and continues until the field is at a market ready point, which is generally 100 days. Once the field is at market ready (market ready being the point where the heads are harvestable as a vegetable for sale) the seed production starts. Market ready heads are generally seen in the female and first male in late April to early May of the year following transplanting. The fully developed heads age and then bolt, which is the extension of individual flower stalks. The nick or timing between the male plants bolting and female plants bolting is now the crucial item watched. The female will only set hybrid seed if pollen is in constant and abundant supply from a male plant. The heads of both the male and female plant can be trimmed to accelerate or slow down the flowering to insure abundant male flowers are available as the female plant flowers. Pollen transfer from the male to the female is done by honeybees, which are commercially supplied. Each acre of seed production requires three to five hives of honeybees. The flowering stage will last sixty to eighty days.

The flowering period is followed by the maturation of the seed within seedpods. The maturation period of 40 to 60 days is checked by monitoring the seed development, as it goes from green and water filled, to the dough stage ending with the seed turning from green to brown in color. A judgment call is made, measuring the number of the mature seeds versus seeds yet completed. When the majority of the seed is mature the female plants are cut by hand and laid in rows (windrowed) to dry down for combining. Ten to twenty days are needed for the plants to dry down.

Combining is a process, which entails the use of a large harvest machine that lifts the broccoli plants from the ground and grinds them for seed preparation. The plant material is cleaned away from the seed by screens and air, leaving only seed. Combining is the initiation of the seed re-conditioning process. Once combined or harvested, the seed is sent to a mill, which further cleans the seed, separates the clean seed by size and weight within a size. All testing for purity, disease, germination, and percent hybridity is done on the clean, sized, and weighted seed. If the seed passes the testing it is canned for sale.

The above method describes the seed production methods for the specific hybrids H7007, H7009, H7022, H2061, H2088, H7021R and H7028 and generally is the method used for all other hybrid broccoli seed production. Hybrid seeds H7007, H7009 H7022, H2061, H2088, H7021R and H70028 were produced by crossing corresponding male lines with 393-2-19 as follows:

H7007=393-2-19×male 7007
H7009=393-2-19×male 7009
H7022=393-2-19×male 5580-2 (same derivation as 7770)
H2061=393-2-19×male 1551 (same derivation as 7881)
H2088=393-2-19 male 7009
H7021R=5580 (same derivation as 7770)×393-2-19
H7028=393-2-19×male 7028

Comparative Studies

Several studies have been performed to compare and contrast the broccoli lines of this invention with commercially available broccoli lines.

Comparative Analysis Study #1

In study #1, the following broccoli lines were analyzed: Hybrid 7007, hybrid 7008, hybrid 7022, hybrid 7028, male 7007, male 7009, male 7022, male 7028, hybrid 393-2-19, hybrid 393-2-47, Marathon and Pinnacle. Marathon and Pinnacle are commercially available broccoli hybrids. Hybrid 7022 resulted from a cross between 393-12-19 and 5580-2 (393-2-19/5580-2). As indicated above, 5580 is the same derivative as 7770.

Broccoli seeds were sown in the greenhouse. Broccoli seedlings were transplanted to the field on August 8. Daily high and low temperature measurements during the course of study #1 are presented in Table 1. Note that the growing temperatures for study #1 were generally quite warm.

In study #1, the days from direct seeding to 50% harvest; days from transplanting to 50% harvest and the length of the harvest period are shown in Table 2.1. The results indicate that the broccoli lines of this invention have a significantly longer harvest period than the commercially available hybrids Marathon and Pinnacle. A longer period in which the head remains available for harvest offers growers greater flexibility in harvesting and therefore greatly reduces costs. The harvest "holding" ability is due, in part, to heat tolerance.

Table 2.2 shows data summarizing various characteristics of the broccoli plants at harvest. Tables 2.3A and 2.3B show data regarding the characteristics of the outer leaves at harvest. The data indicate that both Pinnacle and Marathon were gray-green in foliage color, which is demonstratively different and less commercially acceptable than the blue green foliage of the heat tolerant lines of the invention.

Table 2.4A–2.4D show characteristics of the broccoli heads at market maturity. Table 2.5 shows flower color.

Table 2.6 shows resistance to various environmental conditions, undesirable characteristics of broccoli and diseases. Of particular importance is that the commercially available varieties Marathon and Pinnacle are much more susceptible to downy mildew virus as compared to the broccoli lines of the invention.

Table 2.7 shows heat tolerance data. Of particular relevance is the low heat tolerance of the commercially available varieties Marathon and Pinnacle as compared to the broccoli lines of this invention.

TABLE 1

Temperature Data for Study #1

| Date | Temperature (° F.) | | |
|---|---|---|---|
| | Max | min | Average |
| 07/03 | 79 | 47 | 62 |
| 07/04 | 84 | 48 | 63 |
| 07/05 | 75 | 52 | 60 |
| 07/06 | 75 | 52 | 62 |
| 07/07 | 75 | 52 | 61 |
| 07/08 | 71 | 48 | 59 |
| 07/09 | 63 | 54 | 58 |
| 07/10 | 70 | 54 | 59 |
| 07/11 | 73 | 53 | 59 |
| 07/12 | 74 | 52 | 59 |
| 07/13 | 85 | 53 | 65 |
| 07/14 | 87 | 54 | 69 |
| 07/15 | 82 | 50 | 63 |
| 07/16 | 72 | 32 | 62 |
| 07/17 | 76 | 56 | 64 |
| 07/18 | 83 | 58 | 68 |
| 07/19 | 89 | 52 | 69 |
| 07/20 | 83 | 53 | 67 |
| 07/21 | 88 | 53 | 71 |
| 07/22 | 100 | 55 | 78 |
| 07/23 | 99 | 59 | 77 |
| 07/24 | 88 | 56 | 69 |
| 07/25 | 95 | 54 | 72 |
| 07/26 | 81 | 58 | 70 |
| 07/27 | 76 | 55 | 63 |
| 07/28 | 78 | 55 | 62 |
| 07/29 | 75 | 56 | 62 |
| 07/30 | 72 | 56 | 61 |
| 07/31 | 72 | 57 | 62 |
| 08/01 | 82 | 57 | 65 |
| 08/02 | 83 | 56 | 65 |
| 08/03 | 88 | 54 | 68 |
| 08/04 | 83 | 56 | 66 |
| 08/05 | 77 | 56 | 64 |
| 08/06 | 74 | 58 | 64 |
| 08/07 | 79 | 59 | 66 |

TABLE 1-continued

Temperature Data for Study #1

| Date | Temperature (° F.) | | |
|---|---|---|---|
| | Max | min | Average |
| 08/08 | 90 | 56 | 71 |
| 08/09 | 98 | 59 | 74 |
| 08/10 | 109 | 60 | 81 |
| 08/11 | 100 | 61 | 78 |
| 08/12 | 91 | 58 | 70 |
| 08/13 | 83 | 56 | 66 |
| 08/14 | 84 | 52 | 64 |
| 08/15 | 81 | 50 | 62 |
| 08/16 | 86 | 50 | 66 |
| 08/17 | 92 | 53 | 71 |
| 08/18 | 98 | 58 | 75 |
| 08/19 | 97 | 60 | 75 |
| 08/20 | 92 | 57 | 71 |
| 08/21 | 89 | 58 | 68 |
| 08/22 | 74 | 54 | 61 |
| 08/23 | 74 | 53 | 61 |
| 08/24 | 72 | 51 | 61 |
| 08/25 | 69 | 53 | 60 |
| 08/26 | 71 | 52 | 60 |
| 08/27 | 77 | 54 | 63 |
| 08/28 | 81 | 50 | 63 |
| 08/29 | 86 | 51 | 67 |
| 08/30 | 87 | 50 | 67 |
| 08/31 | 83 | 51 | 64 |
| 09/01 | 69 | 54 | 59 |
| 09/02 | 81 | 51 | 61 |
| 09/03 | 91 | 48 | 64 |
| 09/04 | 95 | 52 | 71 |
| 09/05 | 94 | 46 | 72 |
| 09/06 | 95 | 57 | 71 |
| 09/07 | 91 | 55 | 69 |
| 09/08 | 93 | 54 | 71 |
| 09/09 | 98 | 54 | 69 |
| 09/10 | 91 | 58 | 71 |
| 09/11 | 83 | 61 | 69 |
| 09/12 | 89 | 64 | 73 |
| 09/13 | 95 | 68 | 77 |
| 09/14 | 93 | 64 | 75 |
| 09/15 | 77 | 56 | 64 |
| 09/16 | 68 | 56 | 60 |
| 09/17 | 83 | 32 | 70 |
| 09/18 | 85 | 52 | 67 |
| 09/19 | 87 | 55 | 69 |
| 09/20 | 88 | 57 | 68 |
| 09/21 | 76 | 55 | 62 |
| 09/22 | 73 | 53 | 61 |

TABLE 2

Comparative Analysis (Study #1)

2.1. Region of Adaption/Maturity Main Crop at 50% Harvest

| # | I.D. | Region of Adaption | Days from Direct Seeding to 50% Harvest | Days from Transplanting 50% Harvest | Length of Harvest Period in Days |
|---|---|---|---|---|---|
| 1 | Hybrid 7007 | Most regions | 137 | 84 | 7 |
| 2 | Hybrid 7008 | Most regions | 137 | 87 | 6 |
| 3 | Hybrid 7022 | Most regions | 127 | 77 | 6 |
| 4 | Hybrid 7028 | Most regions | 136 | 86 | 6 |
| 5 | Male 7007 | Southwest | 135 | 85 | 3 |
| 6 | Male 7009 | Southwest | 135 | 85 | 4 |
| 7 | Male 7022 | Southwest | 123 | 73 | 5 |
| 8 | Male 7028 | Southwest | 138 | 88 | 5 |
| 9 | Hybrid 393-2-19 | Most regions | 137 | 87 | 8 |
| 10 | Hybrid 393-2-47 | Most regions | 133 | 83 | 6 |
| 11 | Marathon | Most regions | 134 | 84 | 4 |
| 12 | Pinnacle | Southwest | 123 | 73 | 2 |

2.2. Study #1
Plant (At Harvest)

| # | I.D. | Plant Height (cm) | Head Height (cm) | Plant Branches | Plant Habit | Market Class | Lifecycle | Variety Type |
|---|---|---|---|---|---|---|---|---|
| 1 | Hybrid 7007 | 76.5 | 57.5 | Few | Intermediate | Fresh Market/ Processing | Annual | First generation hybrid |
| 2 | Hybrid 7008 | — | — | — | — | — | — | — |
| 3 | Hybrid 7022 | 72 | 51.5 | Few | Spreading | Fresh Market/ Processing | Annual | First generation hybrid |
| 4 | Hybrid 7028 | 82.5 | 57.5 | Few | Intermediate | Fresh Market/ Processing | Annual | First generation hybrid |
| 5 | Male 7007 | 92 | 65 | Few | Intermediate | Fresh Market/ Processing | Annual | Inbred |
| 6 | Male 7009 | 92 | 76 | Few | Intermediate | Fresh Market/ Processing | Annual | Inbred |
| 7 | Male 7022 | 58 | 35 | Few | Compact | Fresh Market/ Processing | Annual | Inbred |
| 8 | Male 7028 | 74.5 | 51 | Few | Intermediate | Fresh Market/ Processing | Annual | Inbred |
| 9 | Inbred 393-2-19 | 62 | 45.5 | Few | Intermediate | Fresh Market/ Processing | Annual | Inbred |
| 10 | Inbred 393-2-47 | 60 | 48.5 | Few | Intermediate | Fresh Market/ Processing | Annual | Inbred |
| 11 | Marathon | 86.5 | 56.5 | Medium | Spreading | Fresh Market/ Processing | Annual | First generation hybrid |
| 12 | Pinnacle | 88.5 | 61.5 | Few | Intermediate | Fresh Market/ Processing | Annual | First generation hybrid |

2.3 A. Study #1
Outer Leaves (At Harvest)

| # | I.D. | # Leaves Per Plant | Leaf Width (cm) | Leaf Length (cm) | Petiole Length (cm) | Leaf Attachment | Wax Presence | Foliage Color |
|---|---|---|---|---|---|---|---|---|
| 1 | Hybrid 7007 | 29 | 20 | 52.5 | 22 | Petiolate | Strong | Blue-green |
| 2 | Hybrid 7008 | — | — | — | — | — | — | — |
| 3 | Hybrid 7022 | 18 | 14 | 41 | 17.5 | Petiolate | Strong | Blue-green |
| 4 | Hybrid 7028 | 25 | 17.5 | 53.5 | 19.5 | Petiolate | Strong | Blue-green |
| 5 | Male 7007 | 30 | 16.5 | 40.5 | 13.5 | Petiolate | Strong | Blue-green |
| 6 | Male 7009 | 26 | 15.5 | 47 | 18 | Petiolate | Strong | Blue-green |
| 7 | Male 7022 | 21 | 23.5 | 48 | 17.5 | Petiolate | Strong | Blue-green |
| 8 | Male 7028 | 34 | 15.5 | 42.5 | 19. | Petiolate | Strong | Blue-green |
| 9 | Inbred 393-2-19 | 23 | 14 | 36 | 11.5 | Petiolate | Strong | Blue-green |
| 10 | Inbred 393-2-47 | 24 | 16.5 | 40 | 17.5 | Petiolate | Strong | Blue-green |
| 11 | Marathon | 50 | 15.5 | 50 | 22 | Petiolate | Intermediate | Grey-green |
| 12 | Pinnacle | 27 | 16 | 46.5 | 21 | Petiolate | Intermediate | Grey-green |

TABLE 2-continued

Comparative Analysis (Study #1)

2.3 B. Study #1
Outer Leaves (At Harvest)

| # | I.D. | Leaf Shape | Leaf Base | Leaf Apex | Leaf Margins | Leaf Veins | Midrib | Blistering | Attitude | Leaf tip Torsion | Upper Side of Leaf Profile |
|---|---|---|---|---|---|---|---|---|---|---|---|
| 1 | Hybrid 7007 | Elliptic | Blunt | Blunt | Slightly wavy | Intermediate | Slightly raised | None | Semi-erect | Weak | Concave |
| 2 | Hybrid 7008 | — | — | — | — | — | — | — | — | — | — |
| 3 | Hybrid 7022 | Narrow elliptic | Blunt | Blunt | Slightly wavy | Intermediate | Slightly raised | None | Semi-erect | None | Planar |
| 4 | Hybrid 7028 | Elliptic | Blunt | Blunt | Slightly wavy | Intermediate | Slightly raised | None | Semi-erect | None | Concave |
| 5 | Male 7007 | Elliptic | Blunt | Blunt | Slightly wavy | Intermediate | Slightly raised | None | Erect | Weak | Concave |
| 6 | Male 7009 | Elliptic | Pointed | Blunt | Slightly wavy | Intermediate | Slightly raised | None | Erect | Intermediate | Planar |
| 7 | Male 7022 | Broad elliptic | Blunt | Blunt | Slightly wavy | Intermediate | Not raised | None | Horizontal/Semi-erect | Weak | Concave |
| 8 | Male 7028 | Elliptic | Blunt | Blunt | Slightly wavy | Intermediate | Slightly raised | None | Erect | None | Concave |
| 9 | Inbred 393-2-19 | Elliptic | Blunt | Blunt | Slightly wavy | Intermediate | Slightly raised | None | Erect | None | Concave |
| 10 | Inbred 393-2-47 | Elliptic | Blunt | Blunt | Slightly wavy | Intermediate | Slightly raised | None | Semi-erect | None | Concave |
| 11 | Marathon | Narrow elliptic | Blunt | Blunt | Very wavy | Intermediate | Slightly raised | None | Horizontal/Semi-erect | None | Concave |
| 12 | Pinnacle | Elliptic | Blunt | Blunt | Slightly wavy | Intermediate | Slightly raised | None | Horizontal | None | Concave |

2.4 A. Study #1
Head (At Market Maturity)

| # | I.D. | Head Diameter (cm) | Head Depth (cm) | Head Weight (gm) | Head Color | Head Shape |
|---|---|---|---|---|---|---|
| 1 | Hybrid 7007 | 17 | 13.5 | 446.3 | Blue/Green | Transverse broad elliptic |
| 2 | Hybrid 7008 | — | — | 352 | — | — |
| 3 | Hybrid 7022 | 15 | 10.5 | 377.2 | Blue/Green | Transverse narrow elliptic |
| 4 | Hybrid 7028 | 15 | 11.5 | 364.4 | Blue/Green | Transverse broad elliptic |
| 5 | Male 7007 | 10 | 8 | 93.7 | Blue/Green | Circular |
| 6 | Male 7009 | 10 | 8.5 | 126.2 | Blue/Green | Transverse broad elliptic |
| 7 | Male 7022 | 15 | 10 | 289.5 | Blue/Green | Transverse narrow elliptic |
| 8 | Male 7028 | 11 | 9.5 | 165.9 | Blue/Green | Circular |
| 9 | Inbred 393-2-19 | 13 | 10 | 325.7 | Blue/Green | Transverse elliptic |
| 10 | Inbred 393-2-47 | 11.5 | 9 | 194.7 | Blue/purple | Transverse broad elliptic |
| 11 | Marathon | 14.5 | 12.5 | 300 | Medium green | Transverse elliptic |
| 12 | Pinnacle | 14 | 9.5 | 274.6 | Medium green | Transverse elliptic |
| 13 | Male 7008 | — | — | 150 | — | — |

2.4 B. Study #1
Head (At Market Maturity)

| # | I.D. | Dome Shape | Head Size | Compactness | Surface Knobbling | Bead Size | Flower Buds |
|---|---|---|---|---|---|---|---|
| 1 | Hybrid 7007 | Semi-domed | Large | Short pedicels (tight) | Fine | Medium | Even in size |
| 2 | Hybrid 7008 | — | — | — | — | — | — |
| 3 | Hybrid 7022 | Very Deeply domed | Large | Short pedicels (tight) | Fine | Medium | Even in size |
| 4 | Hybrid 7028 | Semi-domed | Medium | Short pedicels (tight) | Fine | Medium | Even in size |
| 5 | Male 7007 | Domed | Small | Short pedicels (tight) | Fine | Large | Even in size |
| 6 | Male 7009 | Semi-domed | Small | Medium pedicels | Fine | Large | Even in size |
| 7 | Male 7022 | Very deeply domed | Large | Short pedicels (tight) | Fine | Medium | Even in size |
| 8 | Male 7028 | Domed | Small | Medium pedicels | Fine | Medium | Even in size |
| 9 | Inbred 393-2-19 | Deep domed | Medium | Short pedicels (tight) | Fine | Small | Even in size |
| 10 | Inbred 393-2-47 | Semi-domed | Medium | Short pedicels (tight) | Fine | Medium | Even in size |
| 11 | Marathon | Deep Domed | Medium | Short pedicels (tight) | Medium | Small | Even in size |
| 12 | Pinnacle | Deep Domed | Medium | Medium pedicels | Large | Small | Uneven in size |

2.4 C. Studu #1
Head (At Market Maturity) Anthocyanin Coloration

| # | I.D. | Leaf Axils | Leaf Veins | Leaf Blade | Entire Plant | Leaf Petiole |
|---|---|---|---|---|---|---|
| 1 | Hybrid 7007 | Absent | Absent | Absent | Absent | Absent |
| 2 | Hybrid 7008 | — | — | — | — | — |
| 3 | Hybrid 7022 | Absent | Absent | Absent | Absent | Absent |
| 4 | Hybrid 7028 | Absent | Absent | Absent | Absent | Absent |

TABLE 2-continued

Comparative Analysis (Study #1)

| | | | | | | |
|---|---|---|---|---|---|---|
| 5 | Male 7007 | Absent | Absent | Absent | Absent | Absent |
| 6 | Male 7009 | Absent | Absent | Absent | Absent | Absent |
| 7 | Male 7022 | Absent | Absent | Absent | Absent | Absent |
| 8 | Male 7028 | Absent | Absent | Absent | Absent | Absent |
| 9 | Inbred 393-2-19 | Absent | Absent | Absent | Absent | Absent |
| 10 | Inbred 393-2-47 | Slight Pressure | Absent | Absent | Absent | Absent |
| 11 | Merathon | Absent | Absent | Absent | Absent | Absent |
| 12 | Pinnacle | Absent | Absent | Absent | Absent | Absent |

2.4 D. Study #1
Head (At Market Maturity)

| # | I.D. | Color of Head Leaves | Secondary Heads | Prominence of Secondary Heads | Number of Secondary Heads |
|---|---|---|---|---|---|
| 1 | Hybrid 7007 | Green | Completely Absent | Weak | 0 |
| 2 | Hybrid 7008 | — | — | — | — |
| 3 | Hybrid 7022 | Green | Completely Absent | Weak | 0 |
| 4 | Hybrid 7028 | Green | Basal | Weak | 3 |
| 5 | Male 7007 | Green | Completely Absent | Weak | 0 |
| 6 | Male 7009 | Green | Basal | Weak | 4 |
| 7 | Male 7022 | Green | Completely Absent | Weak | 0 |
| 8 | Male 7028 | Green | Completely Absent | Weak | 0 |
| 9 | Inbred 393-2-19 | Green | Completely Absent | Weak | 0 |
| 10 | Inbred 393-2-47 | Green | Completely Absent | Weak | 0 |
| 11 | Marathon | Green | Auxiliary along entire main stem up to main head | Weak | 3 |
| 12 | Pinnacle | Green | Basal | Weak | 1 |

2.5 Study #1
Flower Color

| # | I.D. | Flower Color | Flower Stalk Color |
|---|---|---|---|
| 1 | Hybrid 7007 | Yellow | Green |
| 2 | Hybrid 7008 | — | — |
| 3 | Hybrid 7022 | Yellow | Green |
| 4 | Hybrid 7028 | Yellow | — |
| 5 | Male 7007 | Yellow | — |
| 6 | Male 7009 | Yellow | — |
| 7 | Male 7022 | Yellow | Green |
| 8 | Male 7028 | Yellow | — |
| 9 | Inbred 393-2-19 | Yellow | Green |
| 10 | Inbred 393-2-47 | Yellow | Green |
| 11 | Marathon | Yellow | Green |
| 12 | Pinnacle | Yellow | Green |

2.6. Study #1
Resistance*

| # | I.D. | Downey Mildew | Buttoning | Blindness | Bolting | Brown Beads | Drought | Cold | Hollow stem | Riceyness | Whiptail |
|---|---|---|---|---|---|---|---|---|---|---|---|
| 1 | Hybrid 7007 | 9 | 8 | 8 | 5 | 9 | 7 | 5 | 8 | 9 | 9 |
| 2 | Hybrid 7008 | — | — | — | — | — | — | — | — | — | — |
| 3 | Hybrid 7022 | 9 | 8 | 8 | 4 | 8 | 7 | 3 | 8 | 9 | 9 |
| 4 | Hybrid 7028 | 9 | 8 | 8 | 4 | 9 | 7 | 4 | 8 | 9 | 9 |
| 5 | Male 7007 | 9 | 8 | 8 | 3 | 9 | 8 | 3 | 9 | 9 | 9 |
| 6 | Male 7009 | 9 | 8 | 8 | 5 | 9 | 8 | 3 | 9 | 9 | 9 |
| 7 | Male 7022 | — | 8 | 8 | 6 | 8 | 8 | 3 | 8 | 9 | 9 |
| 8 | Male 7028 | 9 | 8 | 8 | 5 | 9 | 8 | 3 | 8 | 9 | 9 |
| 9 | Inbred 393-2-19 | 9 | 8 | 8 | 6 | 9 | 8 | 6 | 9 | 9 | 9 |
| 10 | Inbred 393-2-47 | 9 | 8 | 8 | 5 | 9 | 8 | 5 | 9 | 9 | 9 |
| 11 | Marathon | 3 | 8 | 8 | 7 | 8 | 7 | 7 | 8 | 9 | 9 |
| 12 | Pinnacle | 3 | 8 | 8 | 6 | 5 | 5 | 4 | 8 | 5 | 9 |

* 1 = Most susceptible
5 = Intermediate
9 = Most resistant

2.7. Study #1
Heat Tolerance*

| # | I.D. | Heat Tolerance* |
|---|---|---|
| 1 | Hybrid 7007 | 9 |
| 2 | Hybrid 7008 | — |
| 3 | Hybrid 7022 | 8 |
| 4 | Hybrid 7028 | 9 |

TABLE 2-continued

Comparative Analysis (Study #1)

| 5 | Male 7007 | 9 |
| 6 | Male 7009 | 8 |
| 7 | Male 7022 | 7 |
| 8 | Male 7028 | 8 |
| 9 | Inbred 393-2-19 | 8 |
| 10 | Inbred 393-2-47 | 8 |
| 11 | Marathon | 2 |
| 12 | Pinnacle | 4 |

* 1 = Most susceptible
5 = Intermediate
9 = Most tolerant

Comparative Analysis Study #2

In a second study (Study #2) various broccoli lines were analyzed and characterized for heat tolerance. Daily high and low temperature measurements for study #2 are presented in Table 3. As in study #2, the daily temperatures were generally quite warm and on some days hot.

In study #2, the following broccoli lines were analyzed: Hybrid 7007, Hybrid 7009, Hybrid 7028, Male 7007, Male 7009, Male 7028, Inbred 393-2-19, Inbred 393-2-47, Marathon, Pinnacle, 98-2061, 98-2088, Inbred 393-2-32 and 4267-1. 98-2061 results from a cross between 393-2-19 and 1551 (393-2-19/1551). As indicated above, 1551 is the same derivative as 7881. The line 98-2088 results from across between 393-2-19 and M7009 (393-2-19/1551). Line 2192 is derived from the same line as 4267-1.

In study #2, broccoli seeds were sown in the greenhouse on April 27. Broccoli seedlings were transferred to the field on June 13.

The comparative data collected in study #2 are shown in Table 4.

Table 4.1 shows the length of the harvest period, the plant and head height at harvest, the type of plant branches and the plant habit at harvest. Of particular relevance is that the broccoli plants of this invention have a significantly longer harvest period than the commercially available hybrids Marathon and Pinnacle. A longer harvest period offers growers greater flexibility in harvesting and therefore greatly reduces costs.

Tables 4.2A–4.2C show characteristics of outer leaves at harvest. Tables 4.3A–4.3B and 4.4A show characteristics of the harvested broccoli heads. Table 4.5 shows heat tolerance data.

Of particular relevance is the data in Table 4.5, which shows that the broccoli plants of this invention are heat tolerant whereas the commercially available varieties are not.

TABLE 3

Temperature Data for Study #2

| Date | Temperature (° F.) | | |
|---|---|---|---|
| | Max | min | Average |
| 08/08 | 75 | 57 | 63 |
| 08/09 | 81 | 60 | 66 |
| 08/10 | 77 | 58 | 65 |
| 08/11 | 78 | 57 | 65 |
| 08/12 | 79 | 53 | 63 |
| 08/13 | 78 | 55 | 63 |
| 08/14 | 83 | 54 | 64 |
| 08/15 | 77 | 56 | 62 |

TABLE 3-continued

Temperature Data for Study #2

| Date | Temperature (° F.) | | |
|---|---|---|---|
| | Max | min | Average |
| 08/16 | 73 | 56 | 63 |
| 08/17 | 89 | 53 | 63 |
| 08/18 | 83 | 54 | 66 |
| 08/19 | 82 | 59 | 69 |
| 08/20 | 77 | 59 | 66 |
| 08/21 | 87 | 59 | 69 |
| 08/22 | 85 | 56 | 70 |
| 08/23 | 83 | 59 | 69 |
| 08/24 | 82 | 62 | 70 |
| 08/25 | 83 | 57 | 68 |
| 08/26 | 83 | 57 | 68 |
| 08/27 | 83 | 51 | 70 |
| 08/28 | 83 | 56 | 69 |
| 08/29 | 84 | 59 | 69 |
| 08/30 | 82 | 55 | 67 |
| 08/31 | 83 | 59 | 70 |
| 09/01 | 84 | 59 | 70 |
| 09/02 | 81 | 56 | 68 |
| 09/03 | 85 | 59 | 69 |
| 09/04 | 95 | 59 | 73 |
| 09/05 | 87 | 58 | 70 |
| 09/06 | 80 | 55 | 65 |
| 09/07 | 88 | 53 | 66 |
| 09/08 | 86 | 59 | 69 |
| 09/09 | 82 | 55 | 66 |
| 09/10 | 80 | 54 | 66 |
| 09/11 | 79 | 58 | 67 |
| 09/12 | 78 | 54 | 65 |
| 09/13 | 78 | 53 | 63 |
| 09/14 | 79 | 54 | 65 |
| 09/15 | 80 | 56 | 66 |
| 09/16 | 85 | 51 | 68 |
| 09/17 | 79 | 54 | 66 |
| 09/18 | 78 | 54 | 64 |
| 09/19 | 82 | 48 | 63 |
| 09/20 | 88 | 51 | 68 |
| 09/21 | 89 | 51 | 66 |
| 09/22 | 87 | 49 | 66 |
| 09/23 | 102 | 54 | 75 |
| 09/24 | 97 | 59 | 74 |
| 09/25 | 87 | 61 | 72 |
| 09/26 | 80 | 57 | 67 |
| 09/27 | 87 | 52 | 68 |
| 09/28 | 95 | 52 | 73 |
| 09/29 | 90 | 59 | 69 |
| 09/30 | 94 | 54 | 65 |
| 10/01 | 74 | 56 | 63 |
| 10/02 | 76 | 57 | 64 |
| 10/03 | 83 | 51 | 66 |
| 10/04 | 81 | 51 | 65 |
| 10/05 | 83 | 50 | 64 |
| 10/06 | 69 | 49 | 59 |
| 10/07 | 70 | 46 | 57 |

TABLE 3-continued

Temperature Data for Study #2

| Date | Temperature (° F.) | | |
|---|---|---|---|
| | Max | min | Average |
| 10/08 | 72 | 43 | 57 |
| 10/09 | 65 | 52 | 60 |
| 10/10 | 62 | 44 | 53 |
| 10/11 | 68 | 44 | 55 |
| 10/12 | 74 | 44 | 57 |
| 10/13 | 83 | 42 | 61 |
| 10/14 | 89 | 44 | 65 |
| 10/15 | 95 | 49 | 68 |
| 10/16 | 96 | 50 | 68 |
| 10/17 | 87 | 50 | 64 |
| 10/18 | 81 | 46 | 59 |
| 10/19 | 64 | 49 | 56 |
| 10/20 | 70 | 49 | 57 |
| 10/21 | 74 | 45 | 55 |
| 10/22 | 70 | 45 | 54 |
| 10/23 | 68 | 49 | 57 |
| 10/24 | 72 | 42 | 55 |
| 10/25 | 75 | 38 | 56 |
| 10/26 | 79 | 40 | 57 |
| 10/27 | 75 | 42 | 56 |

TABLE 4

COMPARATIVE ANALYSIS Study #2

4.1. Maturity: Main Crop at 50% Harvest/Plant At Harvest

| # | I.D. | Length of Harvest Period (Days) | Plant Height (inches) | Head Height (inches) | Plant Branches | Plant Habit |
|---|---|---|---|---|---|---|
| 1 | Hybrid 7007 | 5 | 30 | 22 | Medium | Spreading |
| 2 | Hybrid 7009 | 5 | 28¼ | 22 | Medium | Spreading |
| 3 | Hybrid 7028 | 4 | 25⅝ | 17 | Medium | Spreading |
| 4 | Male 7007 | 3 | 36 | 33 | Medium | Spreading |
| 5 | Male 7009 | 4 | 37 | 25½ | Many | Spreading |
| 6 | Male 7028 | — | 31 | 23½ | Medium | Spreading |
| 7 | Inbred 393-2-19 | 6 | 27 | 20 | Medium | Spreading |
| 8 | Inbred 393-2-47 | 4.5 | 26 | 20 | Few | Spreading |
| 9 | Marathon | 1 | 30.5 | 20 | Many | Intermediate |
| 10 | Pinnacle | 1 | 30 | 26¾ | Medium | Intermediate |
| 11 | 98-2061 | 5 | 26 | 18 | Medium | Intermediate |
| 12 | 98-2088 | 4 | 29¼ | 23¾ | Medium | Intermediate |
| 13 | Inbred 393-2-32 | 6 | 27 | 18¼ | Medium | Intermediate |
| 14 | 98-2192 | 6 | 28 | 16 | Medium | Spreading |

4.2 A. Study #2
Outer Leaves (At Harvest)

| # | I.D. | # Leaves Per Plant | Leaf Width (inches) | Leaf Length (inches) | Petiole Length (inches) | Length/Width Ratio |
|---|---|---|---|---|---|---|
| 1 | Hybrid 7007 | 23 | 8 | 18¼ | 5 | 2:1 |
| 2 | Hybrid 7009 | 26 | 8 | 17 | 5 | 2:1 |
| 3 | Hybrid 7028 | 22 | 6½ | 16 | 4¾ | 2:1 |
| 4 | Male 7007 | 24 | 10 | 19 | 7 | 2:1 |
| 5 | Male 7009 | 32 | 9 | 21½ | 6¾ | 2:1 |
| 6 | Male 7028 | 18 | 10½ | 22½ | 6½ | 2:1 |
| 7 | Inbred 393-2-19 | 21 | 7 | 16½ | 5½ | 2:1 |
| 8 | Inbred 393-2-47 | 17 | 5¾ | 11¾ | 3½ | 2:1 |
| 9 | Marathon | 32 | 7 | 18 | 8¼ | 2:1 |
| 10 | Pinnacle | 25 | 5⅝ | 14½ | 7¼ | 2:1 |
| 11 | 98-2061 | 19 | 6½ | 16½ | 6¼ | 2:1 |
| 12 | 98-2088 | 28 | 7¼ | 14¾ | 3½ | 2:1 |
| 13 | Inbred 393-2-32 | 21 | 6½ | 19 | 8¼ | 2:1 |
| 14 | 98-2192 | 28 | 8¼ | 18½ | 7¾ | 2:1 |

4.2 B. Study #2
Outer Leaves (At Harvest)

| # | I.D. | Leaf Attachment | Wax Presence | Foliage Color | Leaf Shape | Leaf Base |
|---|---|---|---|---|---|---|
| 1 | Hybrid 7007 | Petiolate | Strong | Medium green | Elliptic | Pointed |
| 2 | Hybrid 7009 | Petiolate | Strong | Mediumgreen | Elliptic | Blunt |
| 3 | Hybrid 7028 | Petiolate | Strong | Medium green | Elliptic | Blunt |
| 4 | Male 7007 | Petiolate | Strong | Medium green | Elliptic | Blunt |
| 5 | Male 7009 | Petiolate | Strong | Medium green | Broad elliptic | Blunt/pointed |
| 6 | Male 7028 | Petiolate | Strong | Medium green | Broad elliptic | Blunt/pointed |

TABLE 4-continued

COMPARATIVE ANALYSIS Study #2

| | | | | | | |
|---|---|---|---|---|---|---|
| 7 | Inbred 393-2-19 | Petiolate | Strong | Medium green | Elliptic | Blunt |
| 8 | Inbred 393-2-27 | Petiolate | Strong | Medium green | Elliptic | Blunt |
| 9 | Marathon | Petiolate | Strong | Blue-green | Elliptic | Blunt |
| 10 | Pinnacle | Petiolate | Strong | Medium green | Narrow elliptic | Blunt |
| 11 | 98-2061 | Petiolate | Strong | Dark green | Elliptic | Blunt |
| 12 | 98-2088 | Petiolate | Strong | Medium green | Narrow elliptic | Blunt |
| 13 | Inbred 393-2-32 | Petiolate | Strong | Medium green | Elliptic | Blunt |
| 14 | 98-2192 | Petiolate | Strong | Dark green | Elliptic | Blunt |

4.2 C. Study #2
Outer Leaves (At Harvest)

| # | I.D. | Leaf Apex | Leaf Margins | Leaf Veins | Attitude | Torsion | Profile |
|---|---|---|---|---|---|---|---|
| 1 | Hybrid 7007 | Blunt | Slightly wavy | Intermediate | Horizontal | Weak | Planer |
| 2 | Hybrid 7009 | Blunt | Slightly wavy | Intermediate | Semi-erect/erect | Weak | Planar |
| 3 | Hybrid 7028 | Blunt | Slightly wavy | Thin | Semi-erect/erect | Weak | Planar |
| 4 | Male 7007 | Blunt | Slightly wavy | Intermediate | Semi-erect/erect | Weak | Planar |
| 5 | Male 7009 | Blunt | Very wavy | Intermediate | Semi-erect/erect | Weak | Planar/convex |
| 6 | Male 7028 | Blunt | Slightiy wavy | Thick | Horizontal/semi-erect | Weak | Planer |
| 7 | Inbred 393-2-19 | Blunt | Slightly wavy | Intermediate | Semi-erect | Weak | Concave |
| 8 | Inbred 393-2-47 | Blunt | Slightly wavy | Intermediate | Horizontal/semi-erect | Weak | Concave/planar |
| 9 | Marathon | Blunt | Very wavy | Intermediate | Horizontal | Intermediate | Concave |
| 10 | Pinnacle | Blunt | Slightly wavy | Intermediate | Semi-erect/erect | Intermediate | Convex |
| 11 | 98-2061 | Blunt | Slightly wavy | Thin | Semi-erect | Weak | Planar |
| 12 | 98-2088 | Blunt | Slightly wavy | Intermediate | Semi-erect/erect | Weak | Concave |
| 13 | Inbred 393-2-32 | Blunt | Slightly wavy | Intermediate | Horizontal | Weak | Plannar |
| 14 | 98-21 92 | Blunt | Slightly wavy | Intermediate | Semi-erect/erect | Weak | Planar/convex |

4.3 A. Study #2.
Head (At Market Maturity)

| # | I.D. | Head Diameter (inches) | Head Depth (inches) | Head Weight (gm) | Color | Head Shape |
|---|---|---|---|---|---|---|
| 1 | Hybrid 7007 | 10 | 5¼ | 904.9 | Blue/green | Transverse elliptic |
| 2 | Hybrid 7009 | 7 | 3¼ | 306.4 | Purple/blue/green | Transverse elliptic |
| 3 | Hybrid 7028 | 4¾ | 3 | 117 | Blue/green | Transverse elliptic |
| 4 | Male 7007 | 4¼ | 2½ | 85.6 | Medium green | Circular |
| 5 | Male 7009 | 3¾ | 2¼ | 103.6 | Dark green/Blue/green | Transverse broad elliptic |
| 6 | Male 7028 | 6 | 3½ | 450.3 | Light purple/dark green | Transverse elliptic |
| 7 | Inbred 393-2-19 | 5 | 3 | 176.3 | Blue/green purple | Transverse elliptic narrow |
| 8 | Inbred 393-2-47 | 4¾ | 2¾ | 136.4 | Light green/purple | Transverse elliptic |
| 9 | Marathon | 4½ | 2¼ | 313.1 | Yellow | Transverse elliptic |
| 10 | Pinnacle | 6¼ | 4¾ | 336.3 | Blue/green | Transverse elliptic |
| 11 | 98-2061 | 5½ | 3 | 184.1 | Blue/green | Transverse broad elliptic |
| 12 | 98-2088 | 5¾ | 3½ | 184.1 | Blue/green/purple | Transverse elliptic |
| 13 | Inbred 393-2-32 | 3¼ | 2½ | 67.2 | Medium green/blue/green | Transverse broad elliptic |
| 14 | 98-2192 | 5½ | 3 | 226.0 | Blue/green | Transverse elliptic |

4.3 B. Study #2
Head (At Market Maturity)

| # | I.D. | Dome Shape | Head Size | Compactness | Surface Knobbling | Beads Size | Flower Buds |
|---|---|---|---|---|---|---|---|
| 1 | Hybrid 7007 | Domed | Large | Medium pedicels | Medium | Medium/large | Even in size |
| 2 | Hybrid 7009 | Deep-domed | Medium | Medium pedicels | Medium | Medium | Even in size |
| 3 | Hybrid 7028 | Semi-domed | Medium | Short pedicels | Medium | Small | Even in size |
| 4 | Male 7007 | Domed | Small | Medium pedicels | Fine | Medium | Even in size |
| 5 | Male 7009 | Deep-domed | Small | Short pedicels | Fine | Small | Even in size |
| 6 | Male 7028 | Deep-domed | Medium | Short pedicels | Medium | Small | Even in size |
| 7 | Inbred 393-2-19 | Deep-domed | Medium | Short pedicels | Medium | Small | Even in size |
| 8 | Inbred 393-2-47 | Domed | Medium | Short pedicels | Medium | Small | Even in size |
| 9 | Marathon | Domed | Small | Short pedicels | Medium | Small | Uneven in size |
| 10 | Pinnacle | Domed | Medium | Long pedicels | Coarse | Large | Uneven in size |
| 11 | 98-2061 | Semi-domed | Medium | Short pedicels | Medium | Small | Even in size |
| 12 | 98-2088 | Semi-domed | Medium | Medium pedicels | Medium | Medium | Even in size |
| 13 | Inbred 393-2-32 | Semi-domed | Small | Short pedicels | Fine | Small | Even in size |
| 14 | 98-2192 | Deep-domed | Medium | Short pedicels | Medium | Small | Even in size |

TABLE 4-continued

COMPARATIVE ANALYSIS Study #2

4.4 A. Study #2
Head (At Market Maturity)

| # | I.D. | Color of Head Leaves | Secondary Heads | Prominence of Secondary Heads | # of Secondary Heads |
|---|---|---|---|---|---|
| 1 | Hybrid 7007 | — | — | — | — |
| 2 | Hybrid 7009 | — | — | — | — |
| 3 | Hybrid 7028 | — | Basal | Weak | 1 |
| 4 | Male 7007 | — | Basal | Weak | 0 |
| 5 | Male 7009 | Green | — | — | — |
| 6 | Male 7028 | — | — | — | — |
| 7 | Inbred 393-2-19 | — | — | — | — |
| 8 | Inbred 393-2-47 | — | — | — | — |
| 9 | Marathon | — | Completely absent | Weak | 0 |
| 10 | Pinnacle | — | Basal | Weak | 3 |
| 11 | 98-2061 | | Basal | Weak | 1 |
| 12 | 98-2088 | | Basal | Intermediate | 4 |
| 13 | Inbred 393-2-32 | | — | — | — |
| 14 | 98-2192 | | Combination | Intermediate | 3 |

4.5. Study #2
Heat Tolerance

| # | I.D. | Heat Tolerance* |
|---|---|---|
| 1 | Hybrid 7007 | 7 |
| 2 | Hybrid 7009 | 8 |
| 3 | Hybrid 7028 | 7 |
| 4 | Male 7007 | — |
| 5 | Male 7009 | 7/8 |
| 6 | Male 7028 | — |
| 7 | Inbred 393-2-19 | 5/6 |
| 8 | Inbred 393-2-47 | 5/6 |
| 9 | Marathon | 2 |
| 10 | Pinnacle | 1 |
| 11 | 98-2061 | 7/8 |
| 12 | 98-2088 | 7 |
| 13 | Inbred 393-2-32 | — |
| 14 | 98-2192 | 8/9 |

*1 = Most susceptible
5 = Intermediate
9 = Most tolerant

Comparative Analysis Study #3

In a third study (Study #3) various broccoli lines were analyzed and characterized for heat tolerance. Lines tested included H7009, H7007, H7028, H7010 H7021R, Marathon, Pinnacle, etc. Lines which include a backslash (/) between the two lines represent a cross between the two lines. The second line on the right side of the backslash, is the "male" line in the cross. The "male" line in the cross is the source of the pollen in the cross. For example 393-2-19/7770 represents a cross between 393-2-19 and 7770 wherein 7770 was the source of the pollen and 393-2-19 was the recipient of the pollen. Single plant selections were made of the crosses. The resulting seed was then selfed. The data presented is summary data based upon an entire row of plants.

As indicated above, H7021R results from a cross between 5580 and 393-2-19 (5580/393-2-19)

Daily high and low temperature measurements for study #3 are presented in Table 5. As in studies #'s 1 and 2, the growth temperatures during study #3 were generally quite warm and sometimes hot.

Various broccoli lines were analyzed for heat tolerance. The heat tolerance data is presented in Table 6.

The commercial hybrids (Marathon, Pinnacle, Premium Crop, Patriot, Laguna, Monte Cristo, Greenbelt, Everest, CMS Liberty, and Landmark) averaged a score of 2.83 for heat tolerance. The new heat tolerant hybrids (7007, 7009, and 7028) that are the subject of this patent application averaged 7.00 for heat tolerance. As discussed above, the heat tolerance scale goes from one (1) to nine (9), with one (1) the most susceptible and nine (9) very highly resistant as described above. In general, ratings of five (5) or below are unmarketable in a heat stress growth condition and represent significant economic loss to the broccoli growers if such a level of heat stress reaction occurs in their broccoli fields.

The broccoli lines from study #3 were also comparatively analyzed for bead size, yield, head shape, extension and maturity. The results are presented in Table 7.

The bead size rating is on a scale of 1–5. A bead size rating of 5.0 represents very, very large beads. A bead size rating of 1.0 represents very, very small beads such as cauliflower beads. A bead size rating of 4.0 represents large beads. An ideal bead size rating is 3.0 to 4.0 with a maximum desirable rating of 3.7 to 3.8. A combination of bead size rating of 3.8 to 4.0 combined with a high bead size uniformity rating is also acceptable.

The yield rating is on a scale of 1 to 10 where a rating of 10 represents a maximum estimated yield for a particular trial. A yield rating of 8.0 compared to a yield rating of 7.0 represents an approximate increase in yield of 50%. While high yields are generally desirable, at the highest yield ratings, hollow core may develop undesirably. A combination of high yield, high heat tolerance (and, therefore head-holding ability) good extension and good uniformity are most desirable. The heat tolerant lines and hybrids of the invention generally exhibited high yields. The high yielding capacity of these lines and hybrids is thought to be due, in part, to an ability to keep increasing head size while maintaining desirable commercial characteristics under heat stress.

The head shape, extension and maturity ratings were on a 0 to 10 scale. Head shape is an important selection criterion for broccoli. Head shape ratings of 7.0 to 8.0 are most desired. A head shape score of 3.0 represents a completely flat to nearly concave head. A head shape score of 4.0 to 5.0 represents a small head not yet approaching a semi-dome. A head shape score of 6.0 represents a semi-dome shaped head. A head shape score of 7.0 represents a good, solid dome. A head shape score of 8.0 represents a deep dome. A head shape score of 9.0 represents a very pointed dome in the shape of a Christmas tree.

Head extension is also an important selection criterion. Head extension is a comparative measurement of the distance between the broccoli head itself and the leaves surrounding the broccoli. If the head is surrounded by leaves, the head is difficult to harvest. Ideally, the head will be extended up above the leaves to permit easy harvesting of the broccoli. An extension rating of 3.0 represents a head that is buried fairly deep within the leaf canopy. A head extension rating of 5.0 represents a plant having a head which extends only slightly above the leaf canopy. A head extension value of 7.0 represents significant extension of the broccoli head out of the canopy. Commercially available broccoli line Marathon has a head extension rating of 6.5–7.0. The beat tolerant broccoli lines of this invention have an extension rating of generally around 7.3. An extension rating of less than 5.0 is undesirable because the head is surrounded by too many leaves making the broccoli difficult to harvest.

Maturity is also an important selection criterion. The smaller the maturity rating number the earlier the harvest date. The larger the maturity rating number the later the harvest date. A late harvest date is indicative of a line which takes longer to reach maturity and, therefore, longer to produce a commercially acceptable head. Generally, a smaller maturity rating number is preferred because the broccoli grower is able to harvest his/her crop sooner. Later maturing lines (with higher maturity rating numbers) are acceptable so long as they continue to produce commercially acceptable heads with a proper head size, coloring, head shape, etc.

Prior art commercially available line Marathon generally has a maturity rating of 5.5/6.0. In contrast, the heat tolerant broccoli lines of this invention generally have a maturity rating of around 6.2.

TABLE 5

Temperature Data for Study #3

| Date | Temperature (° F.) | | |
|---|---|---|---|
| | Max | Min | Average |
| 07/03 | 79 | 47 | 62 |
| 07/04 | 84 | 48 | 63 |
| 07/05 | 75 | 52 | 60 |
| 07/06 | 75 | 52 | 62 |
| 07/07 | 75 | 52 | 61 |
| 07/08 | 71 | 48 | 59 |
| 07/09 | 63 | 54 | 58 |
| 07/10 | 70 | 54 | 59 |
| 07/11 | 73 | 53 | 59 |
| 07/12 | 74 | 52 | 59 |
| 07/13 | 85 | 53 | 65 |
| 07/14 | 87 | 54 | 69 |
| 07/15 | 82 | 50 | 63 |
| 07/16 | 72 | 32 | 62 |
| 07/17 | 76 | 56 | 64 |
| 07/18 | 83 | 58 | 68 |
| 07/19 | 89 | 52 | 69 |
| 07/20 | 83 | 53 | 67 |
| 07/21 | 88 | 53 | 71 |
| 07/22 | 100 | 55 | 78 |
| 07/23 | 99 | 59 | 77 |
| 07/24 | 88 | 56 | 69 |
| 07/25 | 95 | 54 | 72 |
| 07/26 | 81 | 58 | 70 |
| 07/27 | 76 | 55 | 63 |
| 07/28 | 78 | 55 | 62 |
| 07/29 | 75 | 56 | 62 |
| 07/30 | 72 | 56 | 61 |
| 07/31 | 72 | 57 | 62 |
| 08/01 | 82 | 57 | 65 |
| 08/02 | 83 | 56 | 65 |
| 08/03 | 88 | 54 | 68 |
| 08/04 | 83 | 56 | 66 |
| 08/05 | 77 | 56 | 64 |
| 08/06 | 74 | 58 | 64 |
| 08/07 | 79 | 59 | 66 |
| 08/08 | 90 | 56 | 71 |
| 08/09 | 98 | 59 | 74 |
| 08/10 | 109 | 60 | 81 |
| 08/11 | 100 | 61 | 78 |
| 08/12 | 91 | 58 | 70 |
| 08/13 | 83 | 56 | 66 |
| 08/14 | 84 | 52 | 64 |
| 08/15 | 81 | 50 | 62 |
| 08/16 | 86 | 50 | 66 |
| 08/17 | 92 | 53 | 71 |
| 08/18 | 98 | 58 | 75 |
| 08/19 | 97 | 60 | 75 |
| 08/20 | 92 | 57 | 71 |
| 08/21 | 89 | 58 | 68 |
| 08/22 | 74 | 54 | 61 |
| 08/23 | 74 | 53 | 61 |
| 08/24 | 72 | 51 | 61 |
| 08/25 | 69 | 53 | 60 |
| 08/26 | 71 | 52 | 60 |
| 08/27 | 77 | 54 | 63 |
| 08/28 | 81 | 50 | 63 |
| 08/29 | 86 | 51 | 67 |
| 08/30 | 87 | 50 | 67 |
| 08/31 | 83 | 51 | 64 |
| 09/01 | 69 | 54 | 59 |
| 09/02 | 81 | 51 | 61 |
| 09/03 | 91 | 48 | 64 |
| 09/04 | 95 | 52 | 71 |
| 09/05 | 94 | 46 | 72 |
| 09/06 | 95 | 57 | 71 |
| 09/07 | 91 | 55 | 69 |
| 09/08 | 93 | 54 | 71 |
| 09/09 | 98 | 54 | 69 |
| 09/10 | 91 | 58 | 71 |
| 09/11 | 83 | 61 | 69 |
| 09/12 | 89 | 64 | 73 |
| 09/13 | 95 | 68 | 77 |
| 09/14 | 93 | 64 | 75 |
| 09/15 | 77 | 56 | 64 |
| 09/16 | 68 | 56 | 60 |
| 09/17 | 83 | 32 | 70 |
| 09/18 | 85 | 52 | 67 |
| 09/19 | 87 | 55 | 69 |

TABLE 5-continued

Temperature Data for Study #3

| | Temperature (° F.) | | |
|---|---|---|---|
| Date | Max | Min | Average |
| 09/20 | 88 | 57 | 68 |
| 09/21 | 76 | 55 | 62 |
| 09/22 | 73 | 53 | 61 |
| 09/23 | 72 | 52 | 60 |
| 09/24 | 71 | 51 | 59 |
| 09/25 | 65 | 54 | 59 |
| 09/26 | 65 | 49 | 57 |
| 09/27 | 71 | 46 | 46 |
| 09/28 | 73 | 52 | 60 |
| 09/29 | 64 | 48 | 57 |
| 09/30 | 70 | 56 | 59 |
| 10/01 | 63 | 56 | 58 |
| 10/02 | 69 | 47 | 59 |
| 10/03 | 69 | 44 | 55 |
| 10/04 | 76 | 43 | 58 |
| 10/05 | 83 | 44 | 63 |
| 10/06 | 87 | 47 | 65 |
| 10/07 | 78 | 45 | 60 |
| 10/08 | 74 | 51 | 61 |
| 10/09 | 72 | 43 | 57 |
| 10/10 | 75 | 45 | 57 |
| 10/11 | 78 | 40 | 56 |
| 10/12 | 73 | 46 | 58 |
| 10/13 | 75 | 45 | 59 |
| 10/14 | 69 | 32 | 59 |
| 10/15 | 71 | 40 | 54 |
| 10/16 | 74 | 43 | 57 |
| 10/17 | 77 | 39 | 57 |

TABLE 6

Comparative Analysis: Study #3

| # | ID | Heat Tolerance Rating (0–9)** |
|---|---|---|
| 1 | Marathon | 1 |
| 2 | Pinnacle | 3 |
| 4 | H7009 | 8 |
| 5 | Premium Crop | 4– |
| 6 | H7007 | 7+ |
| 8 | H7028 | 6 |
| 9 | Patriot | 1 |
| 10 | H7010 | |
| 11 | Laguna | 5 |
| 12 | H7021R | 5– |
| 13 | Montecristo | 4.1 |
| 14 | Greenbelt | 3– |
| 15 | 393-2-19/7770 | 5– |
| 16 | 393-2-19/7778 | 6– |
| 17 | 393-2-19/7861 | 6 |
| 18 | Sultran | 2.5 |
| 19 | Tierra | 6– |
| 20 | 393-2-19/7864 | |
| 21 | 393-2-19/7865 | 4+ |
| 22 | Everest | 2 |
| 23 | Liberty | 2+ |
| 24 | Marathon | 3 |
| 25 | 7881/M7007 | 7– |
| 26 | 7770-2/393-2-47 | 6 |
| 27 | 7770/7935 | 6 |
| 28 | 7770/7935 | 6 |
| 29 | 7770/7887 | 7– |
| 30 | Landmark | 2 |
| 31 | H7009 | 7 |
| 32 | 8092/7825 | 3 |
| 33 | 8092/7795 | 4+ |
| 34 | 8092/7883 | |
| 35 | 8030/7935 | |
| 36 | 8030/7914 | |
| 37 | H7007 | 7– |
| 38 | Pinnacle | 2+ |
| 39 | Greenbelt | 2 |
| 40 | 393-2-19/1692 | 7– |
| 41 | 393-2-19/1524 | |

**0 = Most susceptible
5 = Intermediate
9 = Most tolerant

TABLE 7

Comparative Analysis: Study #3

| # | ID | Bead Size | Yield | Head Shape | Extension | Maturity |
|---|---|---|---|---|---|---|
| 1 | 7770 | 3.5 | 7.3 | — | — | — |
| 2 | 7778 | 3.7 | 6.1 | 7.0 | 7.5 | 3.7 |
| 3 | 7861 | 3.7 | 4.0 | 7.0 | 7.0 | 5.5 |
| 4 | 7864 | 3.5 | 6.0 | 6.7 | — | 8.0 |
| 5 | 7865 | 3.6 | 7.0 | 6.0 | 7.2 | 7.0 |
| 6 | 7881 | 3.7 | 7.3 | 6.7 | 5.0 | 7.0 |
| 7 | 7887 | 3.8 | 6.7 | 7.0 | 7.7 | 6.7 |
| 8 | 7935 | 3.7 | — | 6.7 | 7.4 | 5.0 |
| 9 | 8092 | 3.5 | 7.7 | 6.0 | 5.3 | 7.0 |
| 10 | 7883 | 3.8 | — | 7.3 | 7.5 | 6.7 |
| 11 | 7914 | 3.6 | — | 5.7 | 7.6 | 6.0 |
| 12 | Pinnacle | 3.7 | 7.0 | 6.3 | 7.0 | 4.0 |

Comparative Analysis Study #4

In a fourth study, various broccoli lines were analyzed and characterized for heat tolerance. Daily high and low temperature measurements for study #3 are presented in Table 8. The maximum daily temperatures during study #4 were generally cooler than the maximum daily temperatures of study #3. In the fourth study, the maximum daily temperature was never greater than 92° F. In contrast, during study #3, the maximum daily temperature was greater than 95° F. on several days.

The heat tolerance ratings for several broccoli lines analyzed during study #4 are present in Table 9. The heat tolerant broccoli lines of the invention consistently exhibited heat tolerance ratings of around 7.0. In contrast, the heat tolerant ratings for the commercially available lines for study #4 averaged around 5.0. The heat tolerance ratings for the commercially available lines were generally higher in study #4 than study #3 because the temperatures were cooler during study #4 than in study #3. Since the commercially available lines were exposed to generally cooler temperatures in study #4, the heat tolerance ratings for these lines were higher during study #4.

In study #4, the heat tolerant broccoli lines were also compared to commercially available lines regarding yield, bead size, head shape, extension and uniformity. The rating scale is the same as that for comparative study #3, Table 7. Uniformity represents a comparative measurement of the similarity between the various plants within a line. High uniformity is desired by growers because it allows them to maximize their harvest efficiency. A minimum uniformity rating of 6.0 to 6.5 is generally viewed as commercially acceptable. A rating of 8.0 represents highly uniform broccoli lines. Uniformity values less than 6.0 are generally viewed as commercially unacceptable. The results are presented in Table 10.

In addition to being heat tolerant, the lines of this invention consistently gave higher head shape and extension ratings than the commercially available lines.

TABLE 8

Temperature Data for Study #4

| Date | Temperature (° F.) Max | Min |
|---|---|---|
| 05/01 | 66 | 50 |
| 05/02 | 65 | 49 |
| 05/03 | 66 | 52 |
| 05/04 | 70 | 41 |
| 05/05 | 83 | 43 |
| 05/06 | 79 | 49 |
| 05/07 | 76 | 51 |
| 05/08 | 75 | 42 |
| 05/09 | 74 | 41 |
| 05/10 | 79 | 42 |
| 05/11 | 74 | 50 |
| 05/12 | 75 | 54 |
| 05/13 | 79 | 42 |
| 05/14 | 68 | 46 |
| 05/15 | 71 | 42 |
| 05/16 | 76 | 42 |
| 05/17 | 82 | 46 |
| 05/18 | 78 | 48 |
| 05/19 | 69 | 51 |
| 05/20 | 67 | 52 |
| 05/21 | 82 | 46 |
| 05/22 | 81 | 49 |
| 05/23 | 75 | 52 |
| 05/24 | 80 | 52 |
| 05/25 | 80 | 53 |
| 05/26 | 75 | 51 |
| 05/27 | 78 | 51 |
| 05/28 | 75 | 51 |
| 05/29 | 61 | 52 |
| 05/30 | 73 | 53 |
| 05/31 | 75 | 51 |
| 06/01 | 70 | 52 |
| 06/02 | 65 | 53 |
| 06/03 | 68 | 48 |
| 06/04 | 68 | 51 |
| 06/05 | 80 | 52 |
| 06/06 | 80 | 53 |
| 06/07 | 75 | 43 |
| 06/08 | 77 | 44 |
| 06/09 | 75 | 44 |
| 06/10 | 81 | 48 |
| 06/11 | 81 | 47 |
| 06/12 | 85 | 51 |
| 06/13 | 84 | 52 |
| 06/14 | 82 | 58 |
| 06/15 | 80 | 57 |
| 06/16 | 84 | 52 |
| 06/17 | 84 | 49 |
| 06/18 | 88 | 51 |
| 06/19 | 84 | 52 |
| 06/20 | 84 | 50 |
| 06/21 | 79 | 54 |
| 06/22 | 86 | 53 |
| 06/23 | 83 | 52 |
| 06/24 | 85 | 54 |
| 06/25 | 83 | 52 |
| 06/26 | 83 | 49 |
| 06/27 | 95 | 49 |
| 06/28 | 99 | 54 |
| 06/29 | 98 | 55 |
| 06/30 | 87 | 51 |
| 07/01 | 87 | 52 |
| 07/02 | 85 | 52 |
| 07/03 | 87 | 52 |
| 07/04 | 87 | 52 |
| 07/05 | 87 | 52 |

TABLE 8-continued

Temperature Data for Study #4

| Date | Temperature (° F.) Max | Min |
|---|---|---|
| 07/06 | 87 | 52 |
| 07/07 | 87 | 51 |
| 07/08 | 88 | 52 |
| 07/09 | 88 | 52 |
| 07/10 | 90 | 52 |
| 07/11 | 90 | 52 |
| 07/12 | 90 | 53 |
| 07/13 | 91 | 55 |
| 07/14 | 90 | 55 |
| 07/15 | 87 | 53 |
| 07/16 | 86 | 54 |
| 07/17 | 88 | 54 |
| 07/18 | 89 | 54 |
| 07/19 | 89 | 54 |
| 07/20 | 89 | 54 |
| 07/21 | 89 | 53 |
| 07/22 | 89 | 53 |
| 07/23 | 87 | 54 |
| 07/24 | 87 | 54 |
| 07/25 | 89 | 54 |
| 07/26 | 89 | 54 |
| 07/27 | 89 | 53 |
| 07/28 | 89 | 54 |
| 07/29 | 90 | 54 |
| 07/30 | 88 | 54 |
| 07/31 | 90 | 54 |
| 08/01 | 90 | 54 |
| 08/02 | 88 | 54 |
| 08/03 | 88 | 54 |
| 08/04 | 88 | 54 |
| 08/05 | 90 | 53 |
| 08/06 | 91 | 54 |
| 08/07 | 90 | 55 |
| 08/08 | 90 | 54 |
| 08/09 | 90 | 55 |
| 08/10 | 88 | 55 |
| 08/11 | 85 | 55 |
| 08/12 | 86 | 54 |
| 08/13 | 85 | 54 |
| 08/14 | 86 | 54 |
| 08/15 | 87 | 54 |
| 08/16 | 88 | 54 |
| 08/17 | 87 | 54 |
| 08/18 | 86 | 54 |
| 08/19 | 86 | 54 |
| 08/20 | 86 | 53 |
| 08/21 | 85 | 52 |
| 08/22 | 85 | 53 |
| 08/23 | 88 | 53 |
| 08/24 | 87 | 53 |
| 08/25 | 87 | 53 |
| 08/26 | 87 | 54 |
| 08/27 | 88 | 53 |
| 08/28 | 89 | 53 |
| 08/29 | 89 | 53 |
| 08/30 | 86 | 54 |
| 08/31 | 87 | 54 |
| 09/01 | 89 | 53 |
| 09/02 | 88 | 53 |
| 09/03 | 88 | 53 |
| 09/04 | 88 | 54 |
| 09/05 | 88 | 54 |
| 09/06 | 86 | 54 |
| 09/07 | 86 | 54 |
| 09/08 | 86 | 53 |
| 09/09 | 86 | 53 |
| 09/10 | 86 | 53 |
| 09/11 | 86 | 53 |
| 09/12 | 85 | 52 |
| 09/13 | 84 | 53 |
| 09/14 | 85 | 53 |
| 09/15 | 85 | 52 |
| 09/16 | 84 | 52 |

TABLE 8-continued

Temperature Data for Study #4

| Date | Temperature (° F.) Max | Temperature (° F.) Min |
|---|---|---|
| 09/17 | 84 | 52 |
| 09/18 | 83 | 52 |
| 09/19 | 84 | 51 |
| 09/20 | 84 | 51 |
| 09/21 | 86 | 50 |
| 09/22 | 86 | 50 |
| 09/23 | 85 | 51 |
| 09/24 | 86 | 52 |
| 09/25 | 84 | 53 |
| 09/26 | 82 | 51 |
| 09/27 | 83 | 53 |
| 09/28 | 83 | 51 |
| 09/29 | 84 | 52 |
| 09/30 | 85 | 51 |
| 10/01 | 84 | 50 |
| 10/02 | 82 | 50 |
| 10/03 | 83 | 50 |
| 10/04 | 83 | 50 |
| 10/05 | 84 | 50 |
| 10/06 | 82 | 50 |
| 10/07 | 80 | 49 |
| 10/08 | 80 | 48 |
| 10/09 | 81 | 49 |
| 10/10 | 80 | 48 |
| 10/11 | 79 | 48 |
| 10/12 | 79 | 48 |
| 10/13 | 80 | 49 |
| 10/14 | 79 | 48 |
| 10/15 | 78 | 47 |
| 10/16 | 78 | 47 |
| 10/17 | 80 | 46 |
| 10/18 | 78 | 46 |
| 10/19 | 76 | 47 |
| 10/20 | 75 | 48 |
| 10/21 | 76 | 47 |
| 10/22 | 77 | 46 |
| 10/23 | 75 | 47 |
| 10/24 | 77 | 46 |
| 10/25 | 75 | 48 |
| 10/26 | 74 | 46 |
| 10/27 | 74 | 45 |
| 10/28 | 71 | 45 |
| 10/29 | 73 | 44 |
| 10/30 | 72 | 43 |
| 10/31 | 73 | 43 |

TABLE 9

Heat Tolerance Data for Study #4

| # | ID | Heat Tolerance Rating* |
|---|---|---|
| 1 | 4243-1 | 7.1 |
| 2 | 4263-1 | 7.2 |
| 3 | 4267-1 | 7.0 |
| 4 |  | 7.2 |
| 5 | 4274-1 | 6.9 |
| 6 | 4274-2 | 6.9 |
| 7 | 4278-1 | 7.4 |
| 8 | 4284-1 | 7.2 |
| 9 | 4285-1 | 6.8 |
| 10 | 4308-2 | 6.8 |
| 11 | 4309-1 | 6.7 |
| 12 | 4318-1 | 6.3 |
| 13 | 4320-1 | 7.0 |
| 14 | 4320-2 | 7.0 |
| 15 | 4321-1 | 7.1 |
| 16 | 4354-1 | 7.2 |
| 17 | 4354-2 | 7.2 |
| 18 | 4355-1 | 6.5 |
| 19 | 4377-1 | 7.1 |
| 20 | 4395-2 | 6.5 |
| 21 | 4412-1 | 6.9 |
| 22 | 4430-1 | 7.4 |
| 23 | 4432-1 | 6.9 |
| 24 | 4437-1 | 7.0 |
| 25 | 4450-1 | 6.6 |
| 26 | 4450-1 | 6.6 |
| 27 | 4460-1 | 7.1 |
| 28 | 4462-1 | 7.2 |
| 29 | 4465-1 | 7.3 |
| 30 | 4476-1 | 7.1 |
| 31 | Pinnacle | 5.0 |
| 32 | Marathon | 5.0 |
| 33 | Greenbelt | 4.5 |
| 34 | 7007 | 7.0 |
| 35 | 4201 | 7.0 |
| 36 | 4208 | 3.0 |
| 37 | 4209 | 6.0 |
| 38 | 4212 | 6.1 |
| 39 | 4219 | 7.0 |
| 40 | 4221 | 6.9 |
| 41 | 4237 | 6.2 |
| 42 | 4280 | 6.1 |
| 43 | 4287 | 6.1 |
| 44 | 4288 | 7.3 |
| 45 | 4289 | 6.0 |
| 46 | 4290 | 6.7 |
| 47 | 4291/4459 | 7.2 |
| 48 | 4301 | 6.5 |
| 49 | 4303 | 7.1 |
| 50 | 4304 | 7.1 |
| 51 | 4317 | 6.4 |
| 52 | 4338 | 4.9 |
| 53 | 4370 | 6.2 |
| 54 | 4415 | 6.7 |
| 55 | 4418 | 5.5 |
| 56 | 4441 | 6.3 |
| 57 | 4442 | 6.3 |
| 58 | 4468 | 6.8 |
| 60 | 4470 | 6.5 |

0 = Most susceptible
5 = Intermediate
9 = Most tolerant

TABLE 10

Yield, Bead Size, Head Shape, Extension and Uniformity Data for Study #4

| # | ID | Yield | Bead Size | Head Shape | Extension | Uniformity |
|---|---|---|---|---|---|---|
| 1 | 4243-1 | 8.8 | 3.6 | 7.0 | 5.5 | 6.5 |
| 2 | 4263-1 | 7.0 | 3.4 | 7.3 | 7.3 | 6.8 |
| 3 | 4267-1 | 6.8 | 3.9 | 6.8 | 7.1 | 6.9 |
| 4 | 4267-1 | 6.9 | 3.9 | 7.1 | 7.2 |  |
| 5 | 4274-1 | 7.2 | 3.5 | 7.3 | 7.5 | 6.8 |
| 6 | 4274-2 | 7.2 | 3.5 | 7.3 | 7.5 | 6.8 |
| 7 | 4278-1 | 7.6 | 3.7 | 7.4 | 7.2 | 6.8 |
| 8 | 4284-1 | 7.3 | 3.5 | 7.4 | 7.5 | 6.9 |
| 9 | 4285-1 | 7.4 | 3.7 | 7.3 | 7.3 | 6.0 |
| 10 | 4308-2 | 7.0 | 3.8 | 6.7 | 7.9 | 6.5 |
| 11 | 4309-1 | 6.9 | 3.7 | 6.5 | 8.2 | 6.4 |
| 12 | 4318-1 |  | 3.6 | 7.5 | 7.6 | 6.9 |
| 13 | 4320-1 | 7.0 | 3.6 | 7.5 | 7.5 | 7.0 |
| 14 | 4320-2 | 7.0 | 3.6 | 7.5 | 7.5 | 7.0 |
| 15 | 4321-1 | 7.0 | 3.7 | 7.6 | 7.2 | 6.9 |
| 16 | 4354-1 | 7.2 | 3.6 | 7.4 | 7.2 | 7.1 |
| 17 | 4354-2 | 7.2 | 3.6 | 7.4 | 7.2 | 7.1 |
| 18 | 4355-1 | 6.8 | 3.9 | 6.1 | 7.8 | 6.5 |
| 19 | 4377-1 | 7.0 | 3.7 | 7.4 | 7.0 | 6.8 |

TABLE 10-continued

Yield, Bead Size, Head Shape, Extension and Uniformity Data for Study #4

| #  | ID        | Yield | Bead Size | Head Shape | Extension | Uniformity |
|----|-----------|-------|-----------|------------|-----------|------------|
| 20 | 4395-2    | 7.0   | 3.7       | 6.8        | 7.2       | 6.8        |
| 21 | 4412-1    | 7.0   | 3.8       | 6.5        | 7.8       | 6.1        |
| 22 | 4430-1    | 7.1   | 3.3       | 7.0        | 7.6       | 6.9        |
| 23 | 4432-1    | 7.4   | 3.5       | 7.2        | 7.5       | 7.0        |
| 24 | 4437-1    | 7.3   | 3.6       | 7.4        | 7.3       | 6.1        |
| 25 | 4450-1    | 7.5   | 3.6       | 7.1        | 7.2       | 6.5        |
| 26 | 4450-2    | 7.5   | 3.6       | 7.1        | 7.2       | 6.5        |
| 27 | 4460-1    | 7.3   | 3.7       | 7.1        | 7.0       | 7.0        |
| 28 | 4462-1    | 7.2   | 3.5       | 7.3        | 7.3       | 6.7        |
| 29 | 4465-1    | 7.4   | 3.5       | 7.2        | 7.1       | 6.2        |
| 30 | 4476-1    | 7.8   | 3.5       | 7.4        | 7.1       | 6.5        |
| 31 | Pinnacle  | 7.2   | 3.6       | 6.0        | 7.2       | 6.9        |
| 32 | Marathon  | 7.3   | 3.3       | 6.0        | 7.0       | 6.7        |
| 33 | Greenbelt | 6.9   | 3.5       | 5.0        | 7.0       | 6.9        |
| 34 | 7007      | 7.5   | 3.8       | 7.3        | 7.1       | 7.0        |

Transgenic Broccoli

The broccoli varieties of this invention can be transformed with useful genes to make heat tolerant transgenic broccoli varieties. Such useful genes include "terminator genes", herbicide resistant genes, insect resistant genes, virus resistant genes and the like.

To introduce isolated genes or a group of genes into the genome of plant cells such as broccoli an efficient host gene vector system is necessary. The foreign genes should be expressed in the transformed plant cells and consistently transmitted (somatically and sexually) to the next generation of cells produced. The vector should be capable of introducing, maintaining and expressing a gene in plant cells, from a variety of sources, including but not limited to plants and animals, bacteria, fungi, yeast or virus. Additionally it should be possible to introduce the vector into a wide variety of plants. The location of the new gene in the plant genome may be important in determining effective gene expression of the genetically engineered plant. In addition, to be effective, the new gene must be passed on to progeny by normal breeding.

Directed genetic modification and expression of foreign genes in dicotyledonous (broad-leafed) plants such as tobacco, broccoli, potato and alfalfa has been shown to be possible using the T-DNA of the tumor-inducing (Ti) plasmid of Agrobacterium tumefaciens. Using recombinant DNA techniques and bacterial genetics, foreign pieces of DNA can be inserted into T-DNA in Agrobacterium. Following infection by the bacterium or Ti plasmid, the foreign DNA is inserted into the host plant chromosomes, thus producing a genetically engineered cell and eventually a genetically engineered plant. A second approach is to introduce root-inducing (Ri) plasmids as the gene vectors.

Transformation of broccoli is well known in the art of molecular biology. For example, in Cao, et al. "Transgenic broccoli with high levels of Bacillus thuringiensis CrylC protein control diamondback moth larvae resistant to CrylA or CrylC," Molecular Breeding 5:131–141 (1999), discloses one method of generation of transgenic broccoli. Such procedures can readily and easily be followed to produce transgenic heat tolerant broccoli plants.

Isolation of Heat Tolerance Genes

Now that heat tolerant broccoli plants have been identified and isolated, the identification of the gene or genes involved in heat tolerance is a straightforward process. One of ordinary skill in the art can identify genes involved in heat tolerance by comparing the DNA of heat tolerant and heat sensitive broccoli plants. One such method of isolating heat tolerance gene is the use of a matrix mill available from Cornell University in Ithaca, N.Y. The use of such a device greatly facilitates the isolation of heat tolerant genes. The device is capable of breaking up 96 small tissue samples simultaneously in sodium hydroxide, releasing the tissue's DNA and denaturing the protein. After the extraction, the tissue sample is then neutralized and the DNA is simultaneously diluted. Once diluted, the DNA is ready for analysis. Using the matrix mill one can compare several heat tolerant to several heat sensitive broccoli lines simultaneously.

In addition to using the matrix mill, basic molecular biological techniques may be utilized by one of ordinary skill in the art to isolate the heat tolerant broccoli gene. Such procedures are outlined in detail in Ausubel, et al. (Eds) (1987) "Current Protocols in Molecular Biology," John Wiley and Sons, New York.

Once the heat tolerant gene or genes are identified in broccoli, the corresponding heat tolerant gene or genes can be isolated in other plants through various hybridization techniques as described in Ausubel, et al.

Furthermore, biological material can be isolated from the seeds and plants of this invention by procedures well known in the art. Such material may include but is not limited to DNA, RNA, protein and carbohydrates.

Deposit Information

Representative of, but not limiting the invention, Applicants have deposited seeds from M7028, M7007, M7009 and 393-2-19 with the American Type Culture Collection.

Applicants have made available to the public without restriction a deposit of at least 2500 seeds of broccoli M7028 with the American Type Culture Collection (ATCC), Rockville, Md. 20852 which has been assigned ATCC number 203530.

Applicants have made available to the public without restriction a deposit of at least 2500 seeds of broccoli M7007 with the American Type Culture Collection (ATCC), Rockville, Md. 20852 which has been assigned ATCC number 203531.

Applicants have made available to the public without restriction a deposit of at least 2500 seeds of broccoli M7009 with the American Type Culture Collection (ATCC), Rockville, Md. 20852 which has been assigned ATCC number 203532.

Applicants have made available to the public without restriction a deposit of at least 2500 seeds of broccoli 393-2-19 with the American Type Culture Collection (ATCC), Rockville, Md. 20852 which has been assigned ATCC number 203533.

The deposits will be maintained in the ATCC depository, which is a public depository, for a period of 30 years, or 5 years after the most recent request, or for the effective life of the patent, whichever is longer, and will be replaced if a deposit becomes nonviable during that period.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

We claim:

1. A broccoli plant or parts of said plant wherein said plant comprises a center head having a diameter of 3 to 10 inches at maturity when said plant is exposed to a maximum daily temperature of 90° F. to 100° F. for 5 consecutive days during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

2. Seed produced by the plant of claim 1, wherein such seed produces a broccoli plant comprising a center head having a diameter of 3 to 10 inches at maturity when said plant is exposed to a maximum daily temperature of 90° F. to 100° F. for at least 5 consecutive days during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

3. A broccoli plant or parts of said plant wherein said plant comprises a center head having a diameter of 3 to 10 inches at maturity when said plant is exposed to a maximum daily temperature of 95° F. to 100° F. for at least 1 day during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

4. Seed produced by the plant of claim 3, wherein such seed produces a broccoli plant comprising a center head having a diameter of 3 to 10 inches at maturity when said plant is exposed to a maximum temperature of 95° F. to 100° F. for at least 1 day during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

5. A broccoli plant or parts of said plant wherein said plant comprises a center head having a diameter of 3 to 10 inches at maturity when said plain is exposed to a maximum temperature of at least 85° F. to 100° F. for at least 15 days during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

6. Seed produced by the plant of claim 5, wherein such seed produces a broccoli plant comprising a center head having a diameter of 3 to 10 inches at maturity when said plant is exposed to a maximum temperature of 85° F. to 100° F. for at least 15 consecutive days during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

7. A broccoli plant or parts of said plant wherein said plant comprises a center head having a diameter of 3 to 10 inches at maturity when said plant is exposed to a maximum temperature of 80° F. to 100° F. for at least 20 days during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

8. Seed produced by the plant of claim 7, wherein such seed produces a broccoli plant comprising a center head having a diameter of 3 to 10 inches at maturity when said plant is exposed to a maximum temperature of 80° F. to 100° F. for at least 20 consecutive days during the bud development phase of said plant wherein said plant exhibit no heat stress symptoms including one or more of the following: non-uniform beads; brown, yellow, light-green or purple colored heads; flat heads; bracts; rapid fracturing of the head, "cateye", and hollow stems.

* * * * *